US010492762B2

(12) United States Patent
Katsuyama

(10) Patent No.: US 10,492,762 B2
(45) Date of Patent: Dec. 3, 2019

(54) ULTRASOUND DIAGNOSTIC DEVICE, ULTRASOUND DIAGNOSTIC METHOD, AND PROGRAM

(71) Applicant: FUJIFILM CORPORATION, Minato-ku, Tokyo (JP)

(72) Inventor: Kimito Katsuyama, Kanagawa (JP)

(73) Assignee: FUJIFILM CORPORATION, Tokyo (JP)

(*) Notice: Subject to any disclaimer, the term of this patent is extended or adjusted under 35 U.S.C. 154(b) by 546 days.

(21) Appl. No.: 14/952,918

(22) Filed: Nov. 26, 2015

(65) Prior Publication Data
US 2016/0074014 A1    Mar. 17, 2016

Related U.S. Application Data

(63) Continuation of application No. PCT/JP2014/061901, filed on Apr. 28, 2014.

(30) Foreign Application Priority Data

Jun. 5, 2013 (JP) ................. 2013-119202

(51) Int. Cl.
A61B 8/08    (2006.01)
A61B 8/00    (2006.01)
G01S 7/52    (2006.01)

(52) U.S. Cl.
CPC .......... A61B 8/5207 (2013.01); A61B 8/4477 (2013.01); A61B 8/463 (2013.01);
(Continued)

(58) Field of Classification Search
CPC ..... A61B 8/485; A61B 8/5223; A61B 8/4477; A61B 8/463; A61B 8/085; A61B 88/469; A61B 8/5207; G01S 7/52036
See application file for complete search history.

(56) References Cited

U.S. PATENT DOCUMENTS

2011/0201932 A1* 8/2011 Duric ................. A61B 8/5207
                                                    600/443
2012/0245467 A1   9/2012 Miyachi

FOREIGN PATENT DOCUMENTS

JP    H1--121039 A    5/1989
JP    2004-97537 A    4/2004
(Continued)

OTHER PUBLICATIONS

Japanese Office Action dated Oct. 18, 2016 in corresponding Japanese Patent Application No. 2013-119202 and a Partial English Translation thereof.

(Continued)

Primary Examiner — Bo Joseph Peng
(74) Attorney, Agent, or Firm — Solaris Intellectual Property Group, PLLC

(57) ABSTRACT

An ultrasound diagnostic apparatus includes: an ultrasound probe; region-of-interest setting means for setting the depth position of a region of interest in a subject; reflection point setting means for setting a plurality of points in a region, which is deeper than the depth position of the region of interest, as reflection points of ultrasound waves transmitted from the ultrasound probe; and sound speed value deriving means for deriving a sound speed value in a region between each of the plurality of reflection points and the ultrasound probe, for each of the plurality of reflection points, based on a reception signal generated when the ultrasound probe receives an ultrasound wave reflected at each of the plurality of reflection points.

16 Claims, 12 Drawing Sheets

(52) U.S. Cl.
CPC .............. *A61B 8/469* (2013.01); *A61B 8/485* (2013.01); *A61B 8/5223* (2013.01); *G01S 7/52036* (2013.01); *A61B 8/085* (2013.01)

(56) References Cited

FOREIGN PATENT DOCUMENTS

| JP | 2012-071037 A | 4/2012 |
|---|---|---|
| JP | 2012-200443 A | 10/2012 |
| JP | 2013-102960 A | 5/2013 |

OTHER PUBLICATIONS

International Search Report issued in International Application No. PCT/JP2014/061901 dated Jul. 22, 2014.
Written Opinion of the ISA issued in International Application No. PCT/JP2014/061901 dated Jul. 22, 2014.

\* cited by examiner

ULTRASOUND DIAGNOSTIC DEVICE, ULTRASOUND DIAGNOSTIC METHOD, AND PROGRAM

CROSS-REFERENCE TO RELATED APPLICATIONS

This application is a continuation application of International Application No. PCT/JP2014/061901, filed Apr. 28, 2014, the disclosure of which is incorporated herein by reference in its entirety. Further, this application claims priority from Japanese Patent Application No. 2013-119202, filed Jun. 5, 2013, the disclosure of which is incorporated herein by reference in its entirety.

BACKGROUND OF THE INVENTION

1. Field of the Invention

The present invention relates to an ultrasound diagnostic apparatus, an ultrasound diagnostic method, and a computer-readable storage medium for generating a tomographic image of a subject by transmitting and receiving ultrasound waves.

2. Description of the Related Art

An ultrasound diagnostic apparatus has been known that transmits an ultrasound wave to a subject from an ultrasound probe and generates a tomographic image of the subject based on a reflected wave from the inside of the subject. In such an ultrasound diagnostic apparatus, it is known that the propagation speed (also referred to as sound speed) of an ultrasound wave propagating through the subject is calculated and this is used in the diagnosis of tissue characteristics (lesions, hardness, and the like) in the subject.

For example, JP2004-97537A discloses an ultrasound diagnostic apparatus configured to calculate a sound speed value in a part of a subject corresponding to a set region of interest, as a tissue characteristic value, based on a reception signal from the inside of the subject and to output information regarding the history of the tissue characteristic value to a monitor.

In addition, JP1989-121039A (JP-H01-121039A) discloses an ultrasound diagnostic apparatus configured to calculate a sound speed value in a subject based on the propagation time from transmission to reception of an ultrasound wave propagating through the subject and to display the calculated sound speed value as the tissue characteristics information of the subject together with an ultrasound tomographic image.

SUMMARY OF THE INVENTION

The above techniques in the related art are based on the assumption that the sound speed in a region of interest is relevant to the tissue characteristics of the region of interest. However, in the diagnosis of tissue characteristics based on the sound speed value, there are the following problems.

That is, when a region of interest is located at a relatively shallow position with respect to the body surface, the accuracy of the calculated sound speed value is generally low. Therefore, when a region of interest is located at a relatively shallow position with respect to the body surface, it is difficult to properly diagnose the tissue characteristics based on the calculated sound speed value.

In addition, it is difficult to diagnose the characteristics of relatively thin tissue based on the sound speed value. For example, in order to determine the presence of a torn portion in a muscle fiber based on the sound speed value, it is necessary to detect a difference between the sound speed value of the muscle fiber and the sound speed value of the torn portion of the muscle fiber. However, since the thickness of muscle tissue is very small, a difference between the sound speed value of the muscle fiber and the sound speed value of the torn portion is unlikely to occur. For this reason, it is difficult to detect the torn portion from the difference between the sound speed values.

The present invention has been made in view of the above, and provides an ultrasound diagnostic apparatus, an ultrasound diagnostic method, and a program capable of diagnosing the tissue characteristics based on the sound speed value in a subject with higher accuracy than in the related art.

According to a first aspect of the present invention, there is provided an ultrasound diagnostic apparatus including: an ultrasound probe that transmits an ultrasound wave toward a subject and receives an ultrasound wave, which is reflected from an inside of the subject, to generate a reception signal; region-of-interest setting means for setting a depth position of a region of interest in the subject; reflection point setting means for setting a plurality of points in a region, which is deeper than the depth position of the region of interest set by the region-of-interest setting means, in the subject, as reflection points of ultrasound waves transmitted from the ultrasound probe; and sound speed value deriving means for deriving a sound speed value in a region between each of the plurality of reflection points and the ultrasound probe, for each of the plurality of reflection points, based on a reception signal generated when the ultrasound probe receives an ultrasound wave reflected at each of the plurality of reflection points set by the reflection point setting means.

According to a second aspect of the present invention, there is provided the ultrasound diagnostic apparatus according to the first aspect that further includes display means for displaying each sound speed value derived by the sound speed value deriving means on a display screen.

According to a third aspect of the present invention, there is provided the ultrasound diagnostic apparatus according to the second aspect in which the display means includes sound speed image generation means for generating a sound speed image in which sound speed values derived by the sound speed value deriving means are displayed in different colors according to magnitude of the sound speed value.

According to a fourth aspect of the present invention, there is provided the ultrasound diagnostic apparatus according to any one of the first to third aspects that further includes diagnostic means for deriving a diagnostic result for the region of interest based on each sound speed value derived by the sound speed value deriving means.

According to a fifth aspect of the present invention, there is provided the ultrasound diagnostic apparatus according to the fourth aspect in which the reflection point setting means sets, as reflection points, a plurality of points along an azimuth direction parallel to an ultrasound wave transmitting and receiving surface of the ultrasound probe.

According to a sixth aspect of the present invention, there is provided the ultrasound diagnostic apparatus according to the fifth aspect in which the diagnostic means derives a diagnostic result based on an average value of the sound speed values, which are derived for the plurality of reflection points by the sound speed value deriving means, and the sound speed value derived for each of the plurality of reflection points by the sound speed value deriving means.

According to a seventh aspect of the present invention, there is provided the ultrasound diagnostic apparatus according to the fourth aspect in which the reflection point setting means sets, as reflection points, a plurality of points along a depth direction crossing an ultrasound wave transmitting and receiving surface of the ultrasound probe.

According to an eighth aspect of the present invention, there is provided the ultrasound diagnostic apparatus according to the seventh aspect in which the diagnostic means derives a difference value between sound speed values for each of at least one or more pairs of two different reflection points among the plurality of reflection points set by the reflection point setting means, and derives a diagnostic result based on the derived difference value.

According to a ninth aspect of the present invention, there is provided the ultrasound diagnostic apparatus according to any one of the first to fourth aspects in which the reflection point setting means sets, as reflection points, a plurality of points along an azimuth direction parallel to an ultrasound wave transmitting and receiving surface of the ultrasound probe and a depth direction crossing the azimuth direction.

According to a tenth aspect of the present invention, there is provided the ultrasound diagnostic apparatus according to any one of the first to ninth aspects in which the ultrasound probe includes a plurality of electro-acoustic transducers and the sound speed value deriving means derives a sound speed value corresponding to each reflection point based on a time until an ultrasound wave reflected at a reflection point set by the reflection point setting means is received by each of the electro-acoustic transducers disposed at different positions.

According to an eleventh aspect of the present invention, there is provided an ultrasound diagnostic method including: setting a depth position of a region of interest in a subject; setting a plurality of points in a region, which is deeper than the set depth position of the region of interest, in the subject, as reflection points of ultrasound waves transmitted from an ultrasound probe; and deriving a sound speed value in a region between each of the plurality of reflection points and the ultrasound probe, for each of the plurality of reflection points, based on a reception signal generated when the ultrasound probe receives an ultrasound wave reflected at each of the plurality of set reflection points.

According to a twelfth aspect of the present invention, there is provided a program causing a computer to function as the region-of-interest setting means, the reflection point setting means, and the sound speed value deriving means in the ultrasound diagnostic apparatus according to any one of the first to tenth aspects.

According to the ultrasound diagnostic apparatus, the ultrasound diagnostic method, and the program according to the present invention, it is possible to diagnose the tissue characteristics based on the sound speed value in a subject with higher accuracy than in the related art.

DESCRIPTION OF THE PREFERRED EMBODIMENTS

Hereinafter, an ultrasound diagnostic apparatus according to an embodiment of the present invention will be described with reference to the diagrams.

First Embodiment

Figure 1:
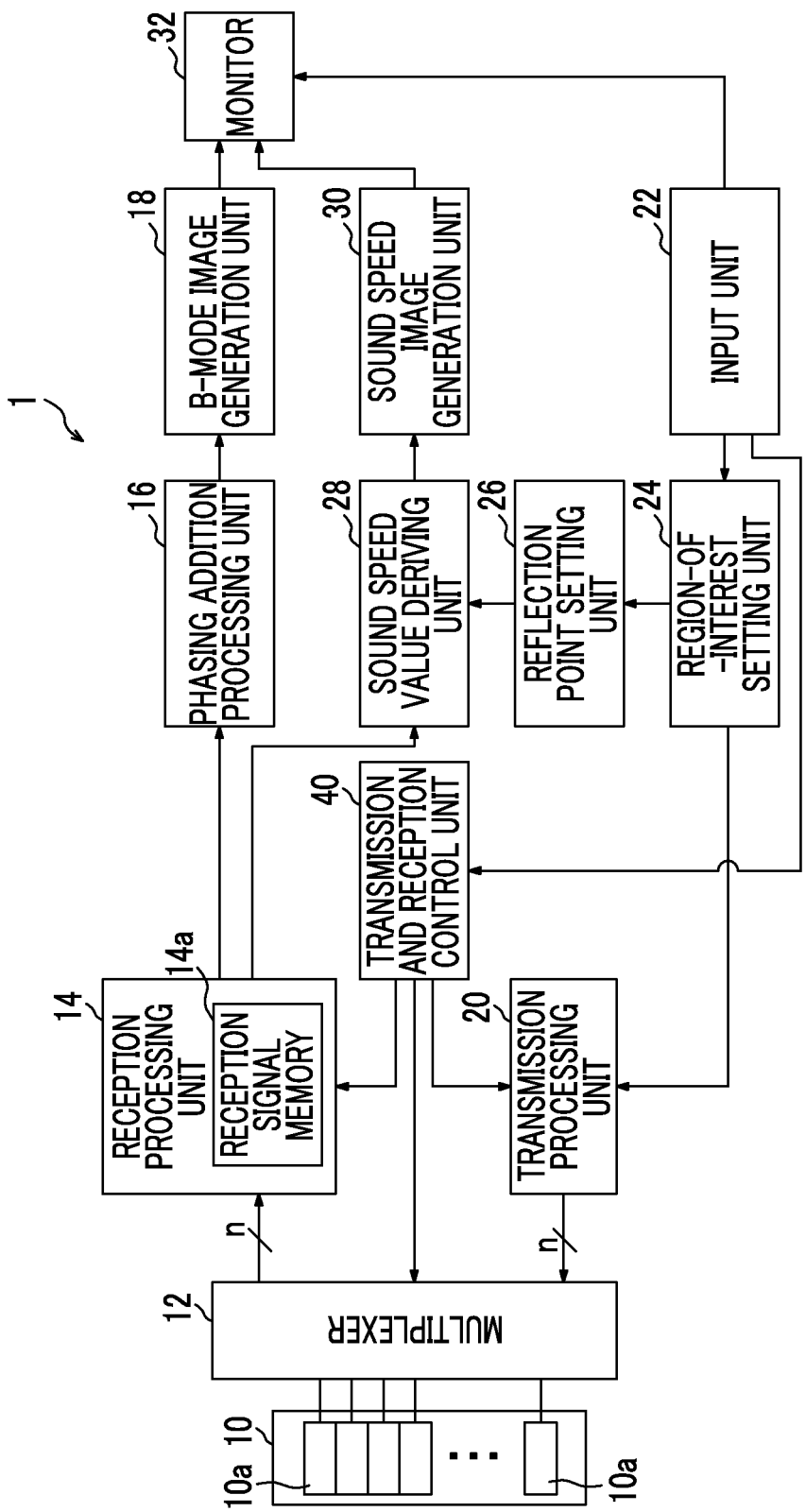
FIG. 1 is a block diagram showing the configuration of an ultrasound diagnostic apparatus according to an embodiment of the present invention.

FIG. 1 is a block diagram showing the configuration of an ultrasound diagnostic apparatus 1 according to a first embodiment of the present invention. An ultrasound probe 10 transmits an ultrasound wave toward a diagnostic part of a subject, and receives a reflected wave (echo) of the ultrasound wave, which is reflected from the inside of the subject, to generate a reception signal. The ultrasound probe 10 includes "m" piezoelectric elements 10a that are arranged linearly, for example. One transmission and reception of ultrasound waves is performed, for example, using a group of "n" (m≥n) adjacent piezoelectric elements selected from the "m" piezoelectric elements 10a. By sequentially shifting the group of "n" piezoelectric elements that are used for the transmission of ultrasound waves, a diagnostic part in the subject is scanned by the ultrasound beam. The ultrasound probe 10 may be of any of scanning types, such as a linear type, a convex type, and a sector type.

The respective piezoelectric elements 10a are connected to a multiplexer 12 through the signal lines of "m" channels. Each of the piezoelectric elements 10a generates an ultrasound wave according to a driving pulse signal that is supplied from a transmission processing unit 20 through the multiplexer 12. In addition, each of the piezoelectric elements 10a generates a reception signal that is an electrical signal by receiving a reflected wave of the ultrasound wave that is reflected from the inside of the subject, and supplies the reception signal to a reception processing unit 14 through the multiplexer 12.

The multiplexer 12 is an electronic switch that selects a group of "n" adjacent piezoelectric elements, which are used for the transmission and reception of ultrasound waves, from the "m" piezoelectric elements 10a of the ultrasound probe 10 according to a control signal supplied from a transmission and reception control unit 40. The multiplexer 12 is connected to the transmission processing unit 20 and the reception processing unit 14 through the signal lines of "n" channels.

The transmission processing unit 20 generates driving pulse signals of the "n" channels at a timing according to the control signal supplied from the transmission and reception control unit 40. In addition, the transmission processing unit 20 gives a relative time difference to the driving pulse signal of each channel in order to perform transmission focusing for converging ultrasound beams on the depth position of a region of interest set by a region-of-interest setting unit 24. The driving pulse signal to which the delay time difference has been given is supplied to each of the "n" piezoelectric elements 10a selected by the multiplexer 12.

The reception processing unit 14 includes an amplifier and an A/D converter (not shown) that are provided for each channel. In the reception processing unit 14, at a timing according to the control signal supplied from the transmission and reception control unit 40, each of reception signals generated by the "n" piezoelectric elements 10a selected by the multiplexer 12 is amplified by the amplifier and is converted into a digital signal by the A/D converter. The reception processing unit 14 includes a reception signal memory 14a that stores the reception signal of each channel converted into the digital signal.

The transmission and reception control unit 40 performs overall control of the timing of the transmission and reception of ultrasound waves by applying a control signal to the multiplexer 12, the transmission processing unit 20, and the reception processing unit 14.

A phasing addition processing unit 16 performs phasing processing for aligning the time phase of the reception signal of each channel by giving a relative time difference to the reception signal of each channel supplied from the reception processing unit 14, that is, reception focusing processing. Timings at which ultrasound waves reflected at a certain reflection point in the subject are incident on the respective piezoelectric elements 10a are not the same. This is because the propagation distance of the reflected wave from the certain reflection point to each piezoelectric element 10a differs depending on each piezoelectric element. The phasing addition processing unit 16 gives a relatively long delay time to a reception signal generated by a piezoelectric element disposed at a position where the distance from the reflection point is relatively short. On the other hand, the phasing addition processing unit 16 gives a relatively short delay time to a reception signal generated by a piezoelectric element disposed at a position where the distance from the reflection point is relatively long. Thus, the phasing addition processing unit 16 performs phasing processing for aligning the time phase of the reception signal of each channel by giving a relative time difference to the reception signal of each channel. Then, the phasing addition processing unit 16 generates a phasing addition signal by adding up the reception signal of each channel after phasing.

A B-mode image generation unit 18 generates an image signal for constructing a so-called B-mode image by converting the signal strength of the phasing addition signal into brightness by performing known filtering processing, Log compression processing, envelope detection processing, sensitivity time control (STC) processing, interpolation processing, scan conversion processing, and the like on the phasing addition signal supplied from the phasing addition processing unit 16.

An input unit 22 is for receiving various kinds of operation input from the user. For example, the input unit 22 is configured to include a pointing device, such as a mouse or a trackball, or input means, such as a keyboard. For example, the user can input a designation input for designating a region of interest (target point) in the subject through the input unit 22. The designation of a region of interest can be performed by inputting the depth position of the region of interest through the input unit 22, for example.

The region-of-interest setting unit 24 stores the depth position of the region of interest of the subject input to the input unit 22, and supplies information indicating the depth position of the region of interest to the transmission processing unit 20 and a reflection point setting unit 26.

The reflection point setting unit 26 sets a plurality of points of a region in the subject, which are deeper than the depth position of the region of interest notified from the region-of-interest setting unit 24, as reflection points for deriving the sound speed value in the subject. A plurality of reflection points set by the reflection point setting unit 26 will be described later.

A sound speed value deriving unit 28 derives a sound speed value V in a region from each of the plurality of reflection points set by the reflection point setting unit 26 to the surface of the ultrasound probe 10, for each reflection point, based on the reception signal of each channel read from the reception processing unit 14. The sound speed value deriving method of the sound speed value deriving unit 28 will be described later.

A sound speed image generation unit 30 generates a sound speed image showing the sound speed value derived for each reflection point by the sound speed value deriving unit 28. For example, the sound speed image generation unit 30 generates an image signal for constructing a sound speed image by assigning a color corresponding to the magnitude of each drawn sound speed value to the pixel position corresponding to the reflection point. The user can check the distribution of the sound speed values corresponding to each reflection point by observing the sound speed image displayed on a monitor 32.

The monitor 32 has a display screen for displaying the B-mode image and the sound speed image based on the image signals supplied from the B-mode image generation unit 18 and the sound speed image generation unit 30. One or both of the B-mode image and the sound speed image are displayed on the display screen based on the operation of the input unit 22 by the user.

Figure 2:
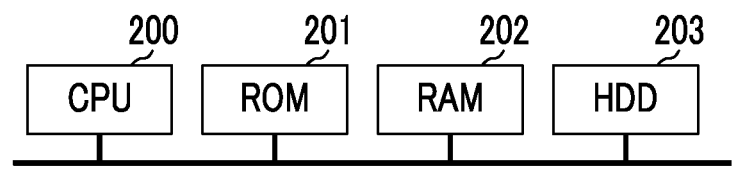
FIG. 2 is a block diagram showing the configuration of a computer included in the ultrasound diagnostic apparatus according to the embodiment of the present invention.

In the ultrasound diagnostic apparatus 1 according to the present embodiment the phasing addition processing unit 16, the B-mode image generation unit 18, the region-of-interest setting unit 24, the reflection point setting unit 26, the sound speed value deriving unit 28, the sound speed image generation unit 30, and the transmission and reception control unit 40 are configured by a computer including a CPU 200, a read only memory (ROM) 201 in which various programs executed by the CPU 200 are stored, a random access memory (RAM) 202 in which data and the like provided for arithmetic processing in the CPU 200 are temporarily stored, and a hard disk drive (HDD) 203 for storing the generated image data and the like, as shown in FIG. 2.

Figure 3:
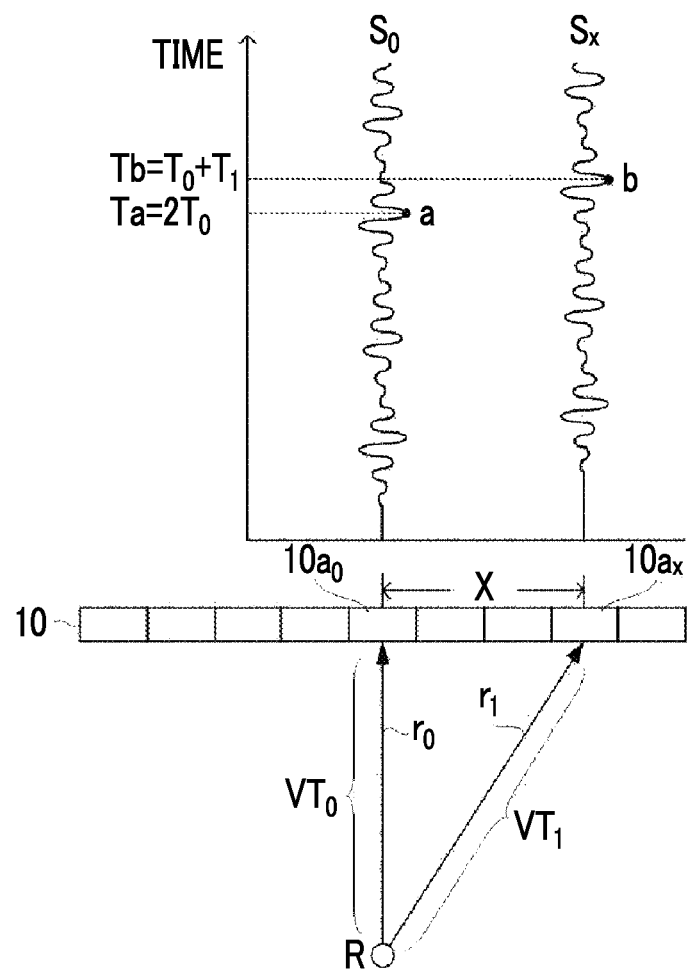
FIG. 3 is a diagram showing a method of deriving a sound speed value in a subject according to the embodiment of the present invention.

Next, a method of deriving the sound speed value in the subject by the sound speed value deriving unit 28 will be described. FIG. 3 is a diagram showing a method of deriving the sound speed value in the subject by the sound speed value deriving unit 28. The sound speed value deriving unit 28 assumes a reflection point R located immediately below an arbitrary piezoelectric element $10a_0$ where the piezoelectric element $10a_0$ receives a reflected wave when a time $T_a$ (=$2T_0$) has elapsed with the transmission time of the ultrasound wave transmitted from the ultrasound probe 10 as the starting point. That is, an ultrasound wave that is transmitted from the ultrasound probe 10 and passes through a center path $r_0$ reaches the reflection point R when a time $T_0$ has elapsed from the transmission time of the ultrasound wave, and an ultrasound wave reflected at the reflection point R reaches the piezoelectric element $10a_0$ when a further time $T_0$ has elapsed through the center path $r_0$ (that is, when the time $T_a$ (=$2T_0$) has elapsed from the transmission time of the ultrasound wave). Here, assuming that the propagation speed (sound speed value) of the ultrasound wave propagating between the reflection point R and the ultrasound probe 10 is V, a distance between the reflection point R and the piezoelectric element $10a_0$ (that is, a path length of the center path $r_0$) can be expressed as $VT_0$.

The sound speed value deriving unit 28 searches for a signal value b, which corresponds to a signal value a at the time $T_a$ (=$2T_0$) in a reception signal $S_0$ generated by the piezoelectric element $10a_0$, on a reception signal $S_x$ generated by a piezoelectric element $10a_x$ that is spaced apart from the piezoelectric element $10a_0$ by a distance X. In this case, the sound speed value deriving unit 28 may search for the corresponding signal value with respect to the reception signals based on the similarity between the waveform of the reception signal $S_0$ and the waveform of the reception signal $S_x$, for example. The sound speed value deriving unit 28 derives a time $T_b$ (=$T_0+T_1$) corresponding to the signal value b on the reception signal $S_x$. That is, an ultrasound wave that is transmitted from the ultrasound probe 10 reaches the reflection point R when the time $T_0$ has elapsed from the transmission time of the ultrasound wave, and an ultrasound wave reflected at the reflection point R reaches the piezoelectric element $10a_x$ when a further time $T_1$ has elapsed through an outer peripheral path $r_1$ rather than the center path $r_0$ (that is, when the time $T_b$ (=$T_0+T_1$) has elapsed from the transmission time of the ultrasound wave). In this case, a distance between the reflection point R and the piezoelectric element $10a_x$ (that is, a path length of the peripheral path $r_1$) can be expressed as $VT_1$.

In the above case, the following Equation (1) is satisfied from the Pythagorean theorem.

$$V^2 T_0^2 + X^2 = V_2 T_1^2 \qquad (1)$$

From the above Equation (1), the sound speed value V can be expressed as the following Equation (2).

$$V = X/(T_1^2 - T_0^2)^{1/2} \qquad (2)$$

Thus, the sound speed value deriving unit 28 derives the sound speed value V in a region between the reflection point R and the ultrasound probe 10 based on the time until the ultrasound wave reflected at the arbitrary reflection point R reaches each of the piezoelectric elements $10a_0$ and $10a_x$ that are spaced from each other by the distance X. The sound speed value V derived in this manner is a sound speed value when the sound speed value in the region between the reflection point R and the ultrasound probe 10 is uniform.

In addition, the apparent depth D of the reflection point R can be expressed by the following Equation (3).

$$D = VT_0 \qquad (3)$$

Next, a specific phenomenon in the case of deriving the sound speed value V according to the above Equation (2) will be described.

Figure 4A:
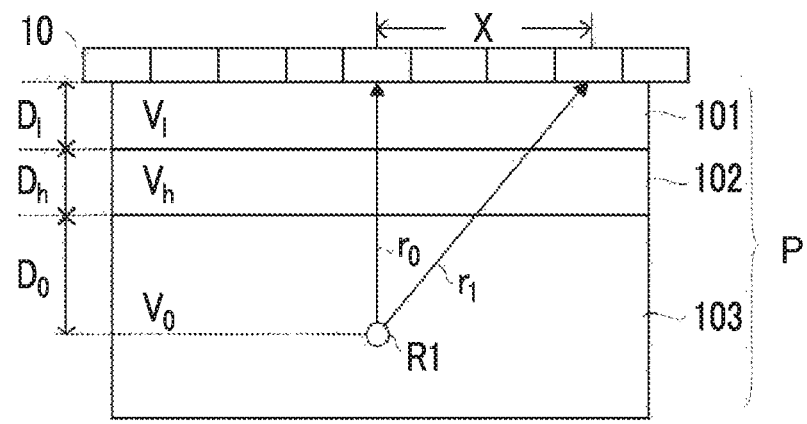
FIG. 4A is a sectional view showing an example of the structure inside the subject.

FIG. 4A shows a case of deriving the sound speed value V in a subject P by bringing the ultrasound probe 10 into contact with the surface of the subject P including a low sound speed region 101 of a sound speed value $V_l$ extending to the top surface of the subject P, a high sound speed region 102 of a sound speed value $V_h$ extending to the bottom of the low sound speed region 101, and a medium sound speed region 103 of a sound speed value $V_0$ extending to the bottom of the high sound speed region 102, and setting a reflection point R1 in the medium sound speed region 103. It is assumed that the thickness of the low sound speed region 101 is $D_l$, the thickness of the high sound speed region 102 is $D_h$, and the distance between the interface of the high sound speed region 102 and the medium sound speed region 103 and the reflection point R1 is $D_0$. In addition, the magnitude relationship between the sound speed values in the sound speed regions 101 to 103 is assumed to be $V_l < V_0 < V_h$. In addition, it is assumed that the low sound speed region 101, the high sound speed region 102, and the medium sound speed region 103 extend in a direction approximately parallel to the ultrasound wave transmitting and receiving surface of the ultrasound probe 10. In this case, the time $T_0$ until the ultrasound wave reflected at the reflection point R1 reaches the surface of the ultrasound probe 10 through the center path $r_0$ can be expressed by the following Equation (4).

$$T_0 = D_0/V_0 + D_h/V_h + D_l/V_l \qquad (4)$$

On the other hand, the time $T_1$ until the ultrasound wave reflected at the reflection point R1 reaches the surface of the ultrasound probe 10 through the peripheral path $r_1$ can be expressed by the following Equation (5). In Equation (5), D is the sum of $D_l$, $D_h$, and $D_0$ ($D = D_l + D_h + D_0$)

$$T_1 = (D_0/V_0 + D_h/V_h + D_l/V_l) \times (D^2 + X^2)^{1/2}/D \qquad (5)$$

By substituting Equations (4) and (5) into Equation (2), the following Equation (6) is derived.

$$1/V = (D_0/D)/V_0 + (D_h/D)/V_h + (D_l/D)/V_l \qquad (6)$$

Equation (6) shows that the sound speed value V derived according to Equation (2) is a value of an ultrasound wave propagating through the sound speed regions 101, 102, and 103, which corresponds to the ratio between the propagation distances of the sound speed regions. That is, when the proportion of the propagation distance of each sound speed region of the ultrasound wave propagating through the center path $r_0$ is the same as the proportion of the propagation distance of each sound speed region of the ultrasound wave propagating through the peripheral path $r_1$ (in other words, when the average sound speed value on the center path $r_0$ is the same as the average sound speed value on the peripheral path $r_1$), the sound speed value V derived according to Equation (2) is the same as the average sound speed value on the center path $r_0$. Here, the average sound speed value is a value obtained by multiplying the sound speed value in each sound speed region on the path by the proportion of each sound speed region on the path and adding up the results. The apparent depth of the reflection point R1 that is derived based on the sound speed value V derived according to Equation (2) is the same as the true depth.

Figure 4B:
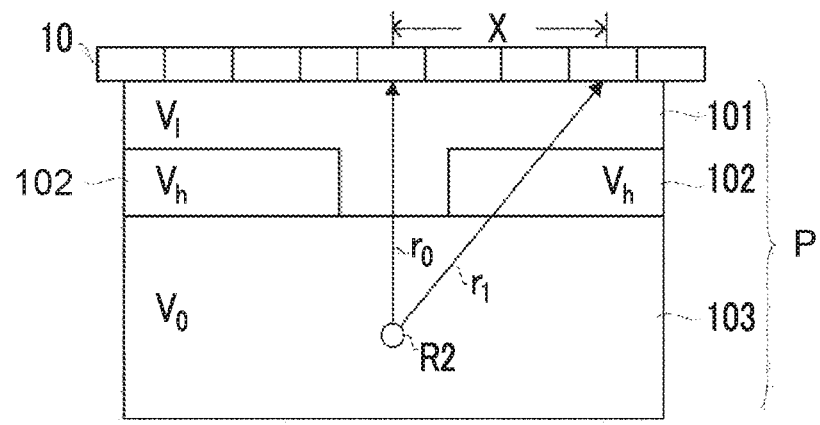
FIG. 4B is a sectional view showing an example of the structure inside the subject.

On the other hand, FIG. 4B shows a case in which the high sound speed region 102 tears and the sound speed value V in the subject P is derived by setting a reflection point R2 immediately below the torn portion of the subject P in which the low sound speed region 101 penetrates into the torn portion. In this case, the ultrasound wave propagating through the center path $r_0$ reaches the surface of the ultrasound probe 10 through the medium sound speed region 103 and the low sound speed region 101 from the reflection point R2. On the other hand, the ultrasound wave propagating through the peripheral path $r_1$ reaches the surface of the ultrasound probe 10 through the medium sound speed region 103, the high sound speed region 102, and the low sound speed region 101 from the reflection point R2. That is, in the case shown in FIG. 4B, the proportion of the propagation distance of the sound speed region of the ultrasound wave propagating through the center path $r_0$ is different from the proportion of the propagation distance of the sound speed region of the ultrasound wave propagating through the peripheral path $r_1$. As a result, the average sound speed value on the center path $r_0$ is smaller than the average sound speed value on the peripheral path $r_1$. In this case, the sound speed value V derived according to Equation (2) is larger than the sound speed value V derived according to Equation (2) in the case shown in FIG. 4A (when the average sound speed value on the center path $r_0$ and the average sound speed value on the peripheral path $r_1$ are the same). This is inconsistent with the situation in which the average sound speed value on the center path $r_0$ in the case shown in FIG. 4B is smaller than that in the case shown in FIG. 4A. In the case shown in FIG. 4B, the sound speed value V derived according to Equation (2) is larger than the average sound speed value on the center path $r_0$, and the apparent depth of the reflection point R2 derived based on the sound speed value V is larger than the true depth.

Figure 5:
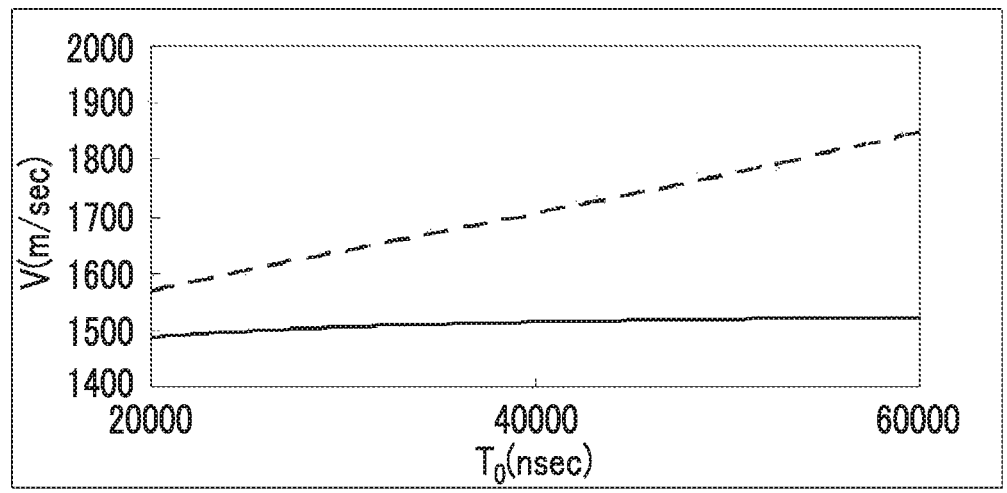
FIG. 5 is a diagram showing a result obtained by simulating the relationship between the depth position of the reflection point and the sound speed value.

FIG. 5 shows a result obtained by simulating the relationship between the propagation time $T_0$ (time until the reflected wave reaches the ultrasound probe through the center path $r_0$ from the reflection point) of the ultrasound wave corresponding to the setting depth of the reflection point (distance from the reflection point to the surface of the ultrasound probe 10) and the sound speed value V derived according to Equation (2). The solid line shown in FIG. 5 corresponds to the case shown in FIG. 4A (when the average sound speed value on the center path $r_0$ and the average sound speed value on the peripheral path $r_1$ are the same), and the dotted line corresponds to the case shown in FIG. 4B (when the average sound speed value on the center path $r_0$ is smaller than the average sound speed value on the peripheral path $r_1$). The simulation was performed by changing the setting depth of the reflection point in the range of 3 cm to 9 cm in a state in which the sound speed value $V_l$ and thickness $D_l$ of the low sound speed region 101 were set to 1450 m/s and 18 mm, the sound speed value $V_h$ and thickness $D_h$ of the high sound speed region 102 were set to 1600 m/s and 2 mm, the sound speed value $V_0$ of the medium sound speed region 103 was set to 1540 m/s, and the distance X between piezoelectric elements for receiving ultrasound waves passing through the center path $r_0$ and the peripheral path $r_1$ was set to 10.56 mm.

In the case shown in FIG. 4A (when the average sound speed value on the center path $r_0$ and the average sound speed value on the peripheral path $r_1$ are the same (solid line in FIG. 5)), as the setting depth of the reflection point increases (that is, as the propagation time $T_0$ of the ultrasound wave passing through the center path $r_0$ from the reflection point R1 increases), the sound speed value V derived according to Equation (2) converges on 1540 m/s equivalent to the sound speed value $V_0$ of the medium sound speed region 103. This is because the proportion of the medium sound speed region 103 on the center path $r_0$ and the peripheral path $r_1$ increases as the setting depth of the reflection point increases. On the other hand, in the case shown in FIG. 4B (when the average sound speed value on the center path $r_0$ is smaller than the average sound speed value on the peripheral path $r_1$ (dotted line in FIG. 5)), as the setting depth of the reflection point increases (that is, as the propagation time $T_0$ of the ultrasound wave passing through the center path $r_0$ from the reflection point R2 increases), a specific phenomenon occurs in which the sound speed value V derived according to Equation (2) increases continuously without converging on $V_0$. In addition, in this case, as the setting depth of the reflection point increases, a difference between the apparent depth of the reflection point derived based on the sound speed value V and the true depth increases.

Figure 6:
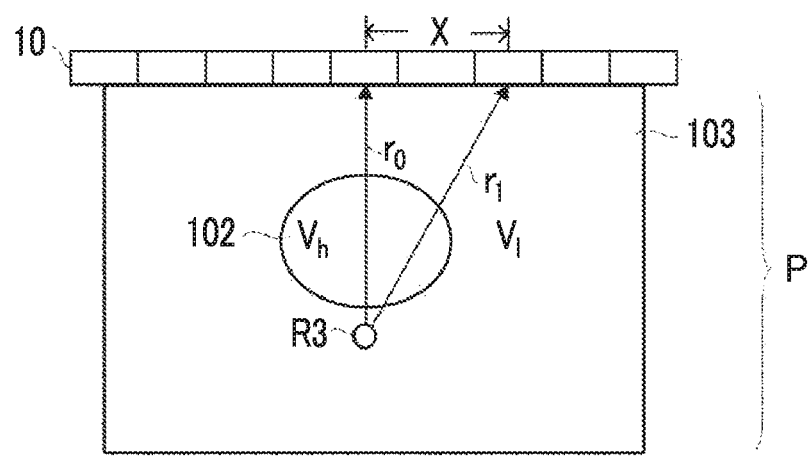
FIG. 6 is a sectional view showing an example of the structure inside the subject.

FIG. 6 shows a case of deriving the sound speed value V by bringing the ultrasound probe 10 into contact with the surface of the subject P including the high sound speed region 102, which has an approximately elliptical section and has the sound speed value $V_h$, and the low sound speed region 101, which extends around the high sound speed region 102 and has the sound speed value $V_l$, setting a reflection point R3 immediately below the high sound speed region 102. Also in this case, the proportion of the propagation distance of the sound speed region of the ultrasound wave propagating through the center path $r_0$ is different from the proportion of the propagation distance of the sound speed region of the ultrasound wave propagating through the peripheral path $r_1$. As a result, also in the case shown in FIG. 6, the average sound speed value on the center path $r_0$ is larger than the average sound speed value on the peripheral path $r_1$. In this case, the sound speed value V derived according to Equation (2) is smaller than the average sound speed value on the center path $r_0$. In addition, the apparent depth of the reflection point R3 that is derived based on the sound speed value V derived according to Equation (2) is smaller than the true depth.

Figure 7:
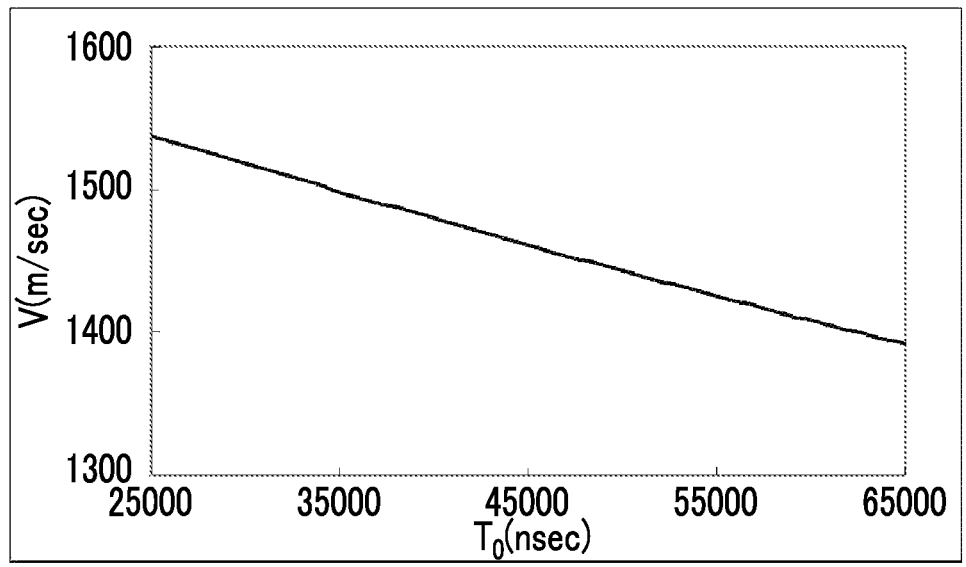
FIG. 7 is a diagram showing a result obtained by simulating the relationship between the depth position of the reflection point and the sound speed value.

FIG. 7 shows a result obtained by simulating the relationship between the propagation time $T_0$ (time until the reflected wave reaches the ultrasound probe through the center path $r_0$ from the reflection point) of the ultrasound wave corresponding to the setting depth of the reflection point in the case shown in FIG. 6 (when the average sound speed value on the center path $r_0$ is larger than the average sound speed value on the peripheral path $r_1$) and the sound speed value V derived according to Equation (2). The simulation was performed by changing the setting depth of the reflection point in the range of 4 cm to 10 cm in a state in which the high sound speed region 102 was made to have a short-axis radius (radius in the depth direction) of 10 mm and a long-axis radius of 15 mm, the sound speed value $V_h$ of the high sound speed region 102 was set to 1600 m/s, the sound speed value $V_l$ of the low sound speed region 101 was set to 1540 m/s, the distance from the center of the high sound speed region 102 having an elliptical shape to the surface of the ultrasound probe 10 was set to 20 mm, and the distance X between piezoelectric elements for receiving ultrasound waves passing through the center path $r_0$ and the peripheral path $r_1$ was set to 10.56 mm. In this case, a specific phenomenon occurs in which the sound speed value V derived according to Equation (2) decreases continuously without converging as the setting depth of the reflection point increases (that is, as the propagation time $T_0$ of the ultrasound wave passing through the center path $r_0$ from the reflection point R3 increases). In addition, in this case, as the setting depth of the reflection point increases, a difference between the apparent depth of the reflection point derived based on the sound speed value V and the true depth increases.

Those described above are summarized as follows.

(i) When the proportion of each sound speed region on the center path $r_0$ is the same as the proportion of each sound speed region on the peripheral path $r_1$ (when the average sound speed value on the center path $r_0$ is the same as the average sound speed value on the peripheral path $r_1$), the sound speed value V derived according to Equation (2) is the same as the average sound speed value on the center path $r_0$ regardless of the setting depth of the reflection point (regardless of the size of the propagation time $T_0$ of the ultrasound wave passing through the center path $r_0$ from the reflection point). In this case, the apparent depth of the reflection point that is derived based on the sound speed value V is the same as the true depth.

(ii) When the proportion of each sound speed region on the center path $r_0$ is different from the proportion of each sound speed region on the peripheral path $r_1$, if the average sound speed value on the center path $r_0$ is smaller than the average sound speed value on the peripheral path $r_1$, the sound speed value V derived according to Equation (2) is larger than the average sound speed value on the center path $r_0$. In this case, as the setting depth of the reflection point increases (as the propagation time $T_0$ of the ultrasound wave passing through the center path $r_0$ from the reflection point increases), the difference between the sound speed value V derived according to Equation (2) and the average sound speed value on the center path $r_0$ increases. In addition, in this case, the apparent depth of the reflection point that is derived based on the sound speed value V is larger than the true depth, and the error increases as the setting depth of the reflection point increases.

(iii) When the proportion of each sound speed region on the center path $r_0$ is different from the proportion of each sound speed region on the peripheral path $r_1$, if the average sound speed value on the center path $r_0$ is larger than the average sound speed value on the peripheral path $r_1$, the sound speed value V derived according to Equation (2) is smaller than the average sound speed value on the center path $r_0$. In this case, as the setting depth of the reflection point increases (as the propagation time $T_0$ of the ultrasound wave passing through the center path $r_0$ from the reflection point increases), the difference between the sound speed value V derived according to Equation (2) and the average sound speed value on the center path $r_0$ increases. In addition, in this case, the apparent depth in the subject that is derived based on the sound speed value V is smaller than the true depth, and the error increases as the propagation time $T_0$ of the ultrasound wave passing through the center path $r_0$ from the reflection point increases.

As described above, the present inventors have found that the specific phenomena described in the above (ii) and (iii) occur if the sound speed value is derived according to Equation (2). The reason why the specific phenomena described in the above (ii) and (iii) occur is that the method of deriving the sound speed value V based on Equation (2) is based on the assumption that the proportion of the propagation distance of each sound speed region of the ultrasound wave propagating through the center path $r_0$ is the same as the proportion of the propagation distance of each sound speed region of the ultrasound wave propagating through the peripheral path $r_1$, as shown in FIG. 4A. Therefore, in the cases shown in FIGS. 4B and 6 in which the above-described assumption is not satisfied, the method of deriving the sound speed value V based on Equation (2) fails. In the cases shown in FIGS. 4B and 6 in which the above-described assumption is not satisfied, it is not possible to calculate an appropriate sound speed value according to Equation (2). Therefore, as is apparent from the simulation results shown in FIGS. 5 and 7, the derived sound speed value V increases or decreases as the setting depth of the reflection point increases (as the propagation time $T_0$ of the ultrasound wave passing through the center path $r_0$ from the reflection point increases).

The ultrasound diagnostic apparatus 1 according to the embodiment of the present invention can easily detect an abnormal part, such as a torn muscle portion or a tumor generated in the subject, using the above-described specific phenomena when deriving the sound speed value V according to Equation (2). Specifically, the ultrasound diagnostic apparatus 1 sets a plurality of points deeper than the depth position of a region of interest as reflection points, derives the sound speed value V in a region between each reflection point and the ultrasound probe 10 according to Equation (2), generates a sound speed image from the derived sound speed values V, and displays the sound speed image on the monitor 32. For example, when a torn muscle portion or a tumor is present in the subject, the sound speed value V corresponding to a reflection point that is set immediately below the torn muscle portion or the tumor is derived as a significantly different value from the sound speed values V corresponding to other reflection points. This is because the average sound speed value on the center path $r_0$ at the reflection point set immediately below the torn muscle portion or the tumor and the average sound speed value on the peripheral path $r_1$ are different due to the presence of the torn muscle portion or the tumor. Therefore, the user can easily determine the presence of a torn muscle portion or a tumor in the subject by observing the sound speed image displayed on the monitor 32.

Hereinafter, the operation of the ultrasound diagnostic apparatus 1 according to the embodiment of the present invention will be described. First, transmission and reception processing when the ultrasound diagnostic apparatus 1 transmits and receives ultrasound waves to generate a reception signal will be described.

Figure 8:
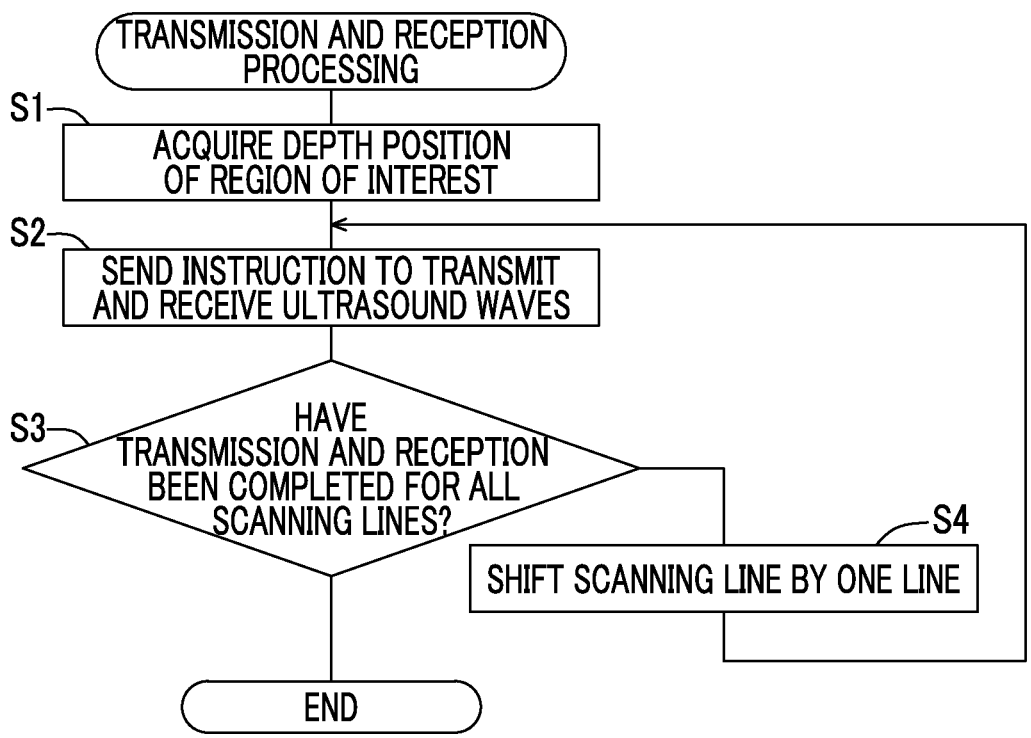
FIG. 8 is a flowchart showing the flow of transmission and reception processing performed in the ultrasound diagnostic apparatus according to the embodiment of the present invention.

FIG. 8 is a flowchart showing the flow of the process in a transmission and reception processing program executed by the CPU 200 of the ultrasound diagnostic apparatus 1. The transmission and reception processing program is stored in the ROM 201 in advance, and is executed, for example, when the user performs a predetermined operation input for the input unit 22.

When the user designates the depth position of a region of interest in the subject by operating the input unit 22, the region-of-interest setting unit 24 stores data indicating the input depth position of the region of interest in the RAM 202 and supplies the data to the transmission processing unit 20 in step S1.

In step S2, the transmission and reception control unit 40 supplies a control signal indicating the start of the transmission and reception of ultrasound waves to the multiplexer 12, the transmission processing unit 20, and the reception processing unit 14. Then, the transmission processing unit 20 generates a driving pulse signal for each channel, and gives a relative time difference to the driving pulse signal of each channel in order to perform transmission focusing on the depth position of the region of interest notified from the region-of-interest setting unit 24. The respective driving pulse signals generated by the transmission processing unit 20 are supplied to the "n" piezoelectric elements 10a selected by the multiplexer 12. As a result, ultrasound beams are transmitted into the subject from the "n" adjacent piezoelectric elements 10a of the ultrasound probe 10.

Echoes obtained by the reflection of the ultrasound beams transmitted from the ultrasound probe 10 are received by the "n" piezoelectric elements 10a selected by the multiplexer 12, for example. In addition, the selection of piezoelectric elements used to receive the echoes is not limited to those described above. Each piezoelectric element 10a converts the reflected echo into a reception signal that is an electrical signal, and supplies the reception signal to the reception processing unit 14 through the multiplexer 12. The reception processing unit 14 performs signal processing including amplification and A/D conversion on each reception signal, and stores the signal-processed reception signal in the reception signal memory 14a, as data of one scanning line, so as to match the identification number of the scanning line.

In step S3, the transmission and reception control unit 40 determines whether or not the transmission and reception of ultrasound waves have been completed for all of a predetermined number of scanning lines. When the transmission and reception control unit 40 determines that the transmission and reception of ultrasound waves have not been completed for all of a predetermined number of scanning lines, the process proceeds to step S4.

In step S4, the transmission and reception control unit 40 supplies a control signal to the multiplexer 12 in order to shift the scanning line by one line. The multiplexer 12 that has received the control signal shifts the piezoelectric elements 10a, which are used for the transmission and reception of ultrasound waves, by one line.

Then, the process returns to step S2, and the transmission and reception of ultrasound waves are performed by each of the piezoelectric elements 10a selected in step S4. By repeatedly performing the processing of steps S2 to S4, a reception signal is acquired for each of the plurality of scanning lines, and the reception signal of each scanning line is stored in the reception signal memory 14a.

When the transmission and reception control unit 40 determines that the transmission and reception of ultrasound waves have been completed for all of a predetermined number of scanning lines in step S3, this routine ends.

Next, a process of generating a B-mode image based on the reception signal acquired by the above transmission and reception processing will be described below.

The phasing addition processing unit 16 aligns the time phase of the reception signal of each channel by reading the reception signal of each channel in one scanning line from the reception signal memory 14a and giving a relative time difference to the read reception signal of each channel. In addition, the phasing addition processing unit 16 performs phasing processing (reception focusing) using the sound speed value in the subject that has been acquired in advance. Then, the phasing addition processing unit 16 generates a phasing addition signal by adding up the reception signal of each channel after the phasing processing. The phasing addition processing unit 16 performs the above processing for each scanning line.

The B-mode image generation unit 18 generates an image signal for constructing a so-called B-mode image by converting the signal strength of the phasing addition signal into brightness by performing known filtering processing, Log compression processing, envelope detection processing, sensitivity time control (STC) processing, interpolation processing, scan conversion processing, and the like on the phasing addition signal of each scanning line supplied from the phasing addition processing unit 16. The image signal generated as described above is supplied to the monitor 32. On the monitor 32, a B-mode image is displayed according to the operation of the input unit 22 by the user.

Next, sound speed image generation processing when the ultrasound diagnostic apparatus 1 generates a sound speed image by deriving the sound speed value V based on the reception signal will be described.

Figure 9:
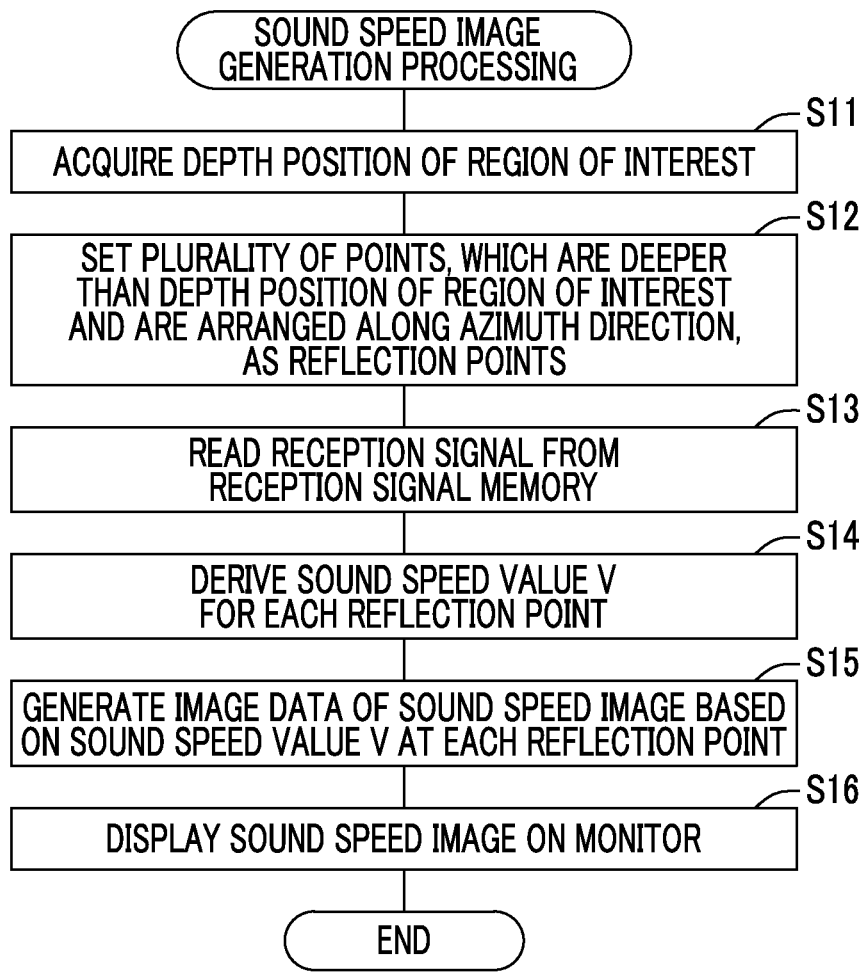
FIG. 9 is a flowchart showing the flow of sound speed image processing performed in the ultrasound diagnostic apparatus according to the embodiment of the present invention.

FIG. 9 is a flowchart showing the flow of the process in a sound speed image generation processing program executed by the CPU 200 of the ultrasound diagnostic apparatus 1. The sound speed image generation processing program is stored in the ROM 201 in advance, and is executed, for example, when the user performs a predetermined operation input for the input unit 22. It is assumed that the above-described transmission and reception processing program (refer to FIG. 8) is executed before the sound speed image generation processing program is executed and a reception signal for deriving the sound speed value V is already stored in the reception signal memory 14a.

When the user designates the depth position of a region of interest in the subject by operating the input unit 22, the region-of-interest setting unit 24 stores data indicating the input depth position of the region of interest in the RAM 202 and supplies the data to the reflection point setting unit 26 in step S11.

In step S12, the reflection point setting unit 26 sets a plurality of points, which are deeper than the depth position of the region of interest notified from the region-of-interest setting unit 24 in step S11, as reflection points for deriving the sound speed value V.

Figure 10:
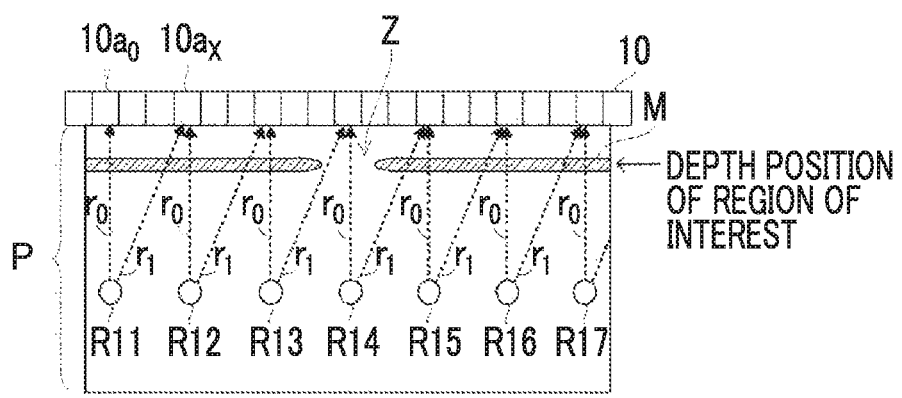
FIG. 10 is a diagram showing the arrangement of reflection points set by a reflection point setting unit according to the embodiment of the present invention.

Here, FIG. 10 is a diagram illustrating the arrangement of reflection points set by the reflection point setting unit 26. In addition, FIG. 10 illustrates a case in which a depth position where a muscle fiber M in the subject P is present is set as the depth position of a region of interest. The reflection point setting unit 26 sets a plurality of points, which are deeper than the set depth position of the region of interest and are arranged along the azimuth direction that is a direction parallel to the ultrasound wave transmitting and receiving surface of the ultrasound probe 10 (direction in which the piezoelectric elements 10a are aligned), as reflection points R11 to R17 for deriving the sound speed value V. Although the seven reflection points R11 to R17 are shown in FIG. 9, the number of reflection points set by the reflection point setting unit 26 can be appropriately changed.

In step S13, the sound speed value deriving unit 28 reads a reception signal corresponding to each scanning line that is stored in the reception signal memory 14a.

In step S14, based on the reception signal of each channel corresponding to each read scanning line, the sound speed value deriving unit 28 derives the sound speed value V according to the above Equation (2) for each of the reflection points R11 to R17 set by the reflection point setting unit 26. For example, in the case of deriving the sound speed value V corresponding to the reflection point R11, the sound speed value deriving unit 28 derives the time $T_0$ until the ultrasound wave reflected at the reflection point R11 reaches the piezoelectric element $10a_0$ located immediately above the reflection point R11. Then, by detecting the signal position corresponding to the reflection point R11 on the reception signal generated in the piezoelectric element $10a_x$ that is spaced part from the piezoelectric element $10a_0$ by the distance X, the sound speed value deriving unit 28 derives the time $T_1$ until the ultrasound wave reflected at the reflection point R11 reaches the piezoelectric element $10a_x$. Then, the sound speed value deriving unit 28 derives the sound speed value V corresponding to the reflection point R11 by substituting the derived times $T_0$ and $T_1$ into Equation (2). The sound speed value deriving unit 28 also derives the sound speed value V corresponding to the reflection points R12 to R17 in the same manner as described above, and supplies the sound speed values V corresponding to the derived reflection points R11 to R17 to the sound speed image generation unit 30.

In step S15, since the sound speed image generation unit 30 has a reference table in which the magnitude of the sound speed value and a color are matched with each other, the sound speed image generation unit 30 searches for a color corresponding to the magnitude of the sound speed value V derived for each of the reflection points R11 to R17 with reference to the reference table. The sound speed image generation unit 30 generates an image signal for constructing a sound speed image by assigning the color corresponding to the magnitude of the sound speed value V of each reflection point to the pixel position of the reflection point. Thus, the sound speed image generation unit 30 generates an image signal of the sound speed image in which the sound speed values derived by the sound speed value deriving unit 28 are displayed in different colors according to the magnitude of each sound speed value.

In step S16, the sound speed image generation unit 30 supplies the image signal of the sound speed image to the monitor 32. As a result, a sound speed image in which the sound speed values corresponding to the respective reflection points have different colors is displayed on the monitor 32.

Here, as shown in FIG. 10, when a torn portion Z is generated in the muscle fiber M, the center path $r_0$ of the ultrasound wave reflected at the reflection point R13 passes through the muscle fiber M, while the peripheral path $r_1$ passes through the torn portion Z without passing through the muscle fiber M. In addition, the center path $r_0$ of the ultrasound wave reflected at the reflection point R14 passes through the torn portion Z without passing through the muscle fiber M, while the peripheral path $r_1$ passes through the muscle fiber M. That is, at the reflection points R13 and R14, the proportion of each sound speed region on the center path $r_0$ is different from the proportion of each sound speed region on the peripheral path $r_1$. On the other hand, since both of the center path $r_0$ and the peripheral path $r_1$ of the ultrasound waves reflected at the reflection points R11, R12, and R15 to R17 pass through the muscle fiber M, the proportion of each sound speed region on the center path $r_0$ and the proportion of each sound speed region on the peripheral path $r_1$ are approximately the same at the reflection points R11, R12, and R15 to R17.

Therefore, the sound speed values V corresponding to the reflection points R13 and R14 derived by the sound speed value deriving unit 28 are significantly different from the sound speed values V corresponding to the reflection points R11, R12, and R15 to R17. In addition, the difference between the sound speed values V increases as the setting depths of the reflection points R11 to R17 increase. By displaying the sound speed image, in which the sound speed values V corresponding to each of the reflection points R11 to R17 have different colors, on the monitor 32, the user can easily check the presence of the torn portion Z and the azimuth position of the torn portion Z.

Thus, according to the ultrasound diagnostic apparatus 1 according to the embodiment of the present invention, an abnormal part, such as a torn portion of the muscle fiber, can be significantly reflected in the sound speed value. Therefore, the diagnosis of tissue characteristics based on the sound speed value in the subject can be performed with higher accuracy than in the related art.

Figure 11:
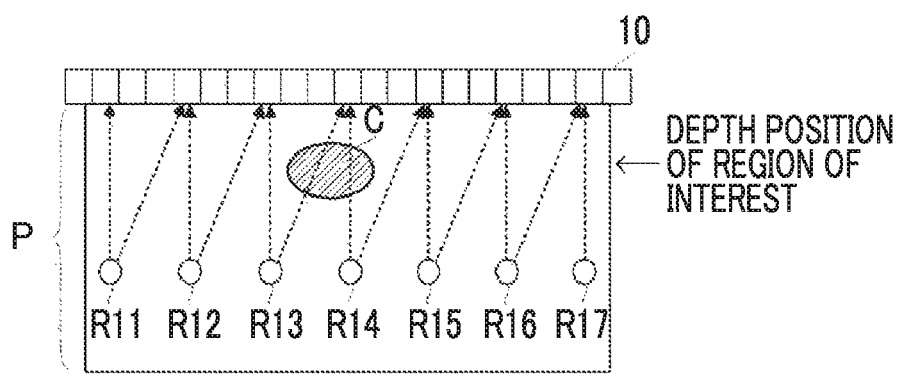
FIG. 11 is a diagram showing the arrangement of reflection points set by a reflection point setting unit according to the embodiment of the present invention.

Although the case of diagnosing the presence of a torn portion of the muscle fiber has been exemplified in the above embodiment, the present invention can also be applied to a case of determining the presence of a tumor C in the subject P as shown in FIG. 11. Here, as the hardness of the tumor C increases, the sound speed value in the tumor C increases, and the difference between the sound speed value in the tumor C and the sound speed value in the tissue around the tumor C increases. According to the ultrasound diagnostic apparatus 1 according to the present embodiment, as the difference between the sound speed value in the tumor C and the sound speed value in the tissue around the tumor C increases, a difference between the sound speed values V corresponding to the reflection points R13 and R14 shown in FIG. 11, at which the center path or the peripheral path of the ultrasound wave passes through the tumor C, and the sound speed values V corresponding to the reflection points R11, R12, and R15 to R17 other than the reflection points R13 and R14 increases. Therefore, according to the ultrasound diagnostic apparatus 1 according to the present embodiment, it is possible to check not only the presence of the tumor C and the azimuth position of the tumor C but also the characteristics of the tumor C, such as the hardness. This can also be utilized for the diagnosis regarding whether or not the tumor C is malignant or benign.

In addition, although the case in which a sound speed image is generated from the sound speed values V derived by the sound speed value deriving unit 28 has been exemplified in the above embodiment, the numerical value of the sound speed value V derived for each reflection point may be displayed on the monitor 32. In this case, the position of the reflection point set by the reflection point setting unit 26 and the sound speed value V for each reflection point may be displayed so as to overlap the B-mode image displayed on the monitor 32.

Second Embodiment

Figure 12:
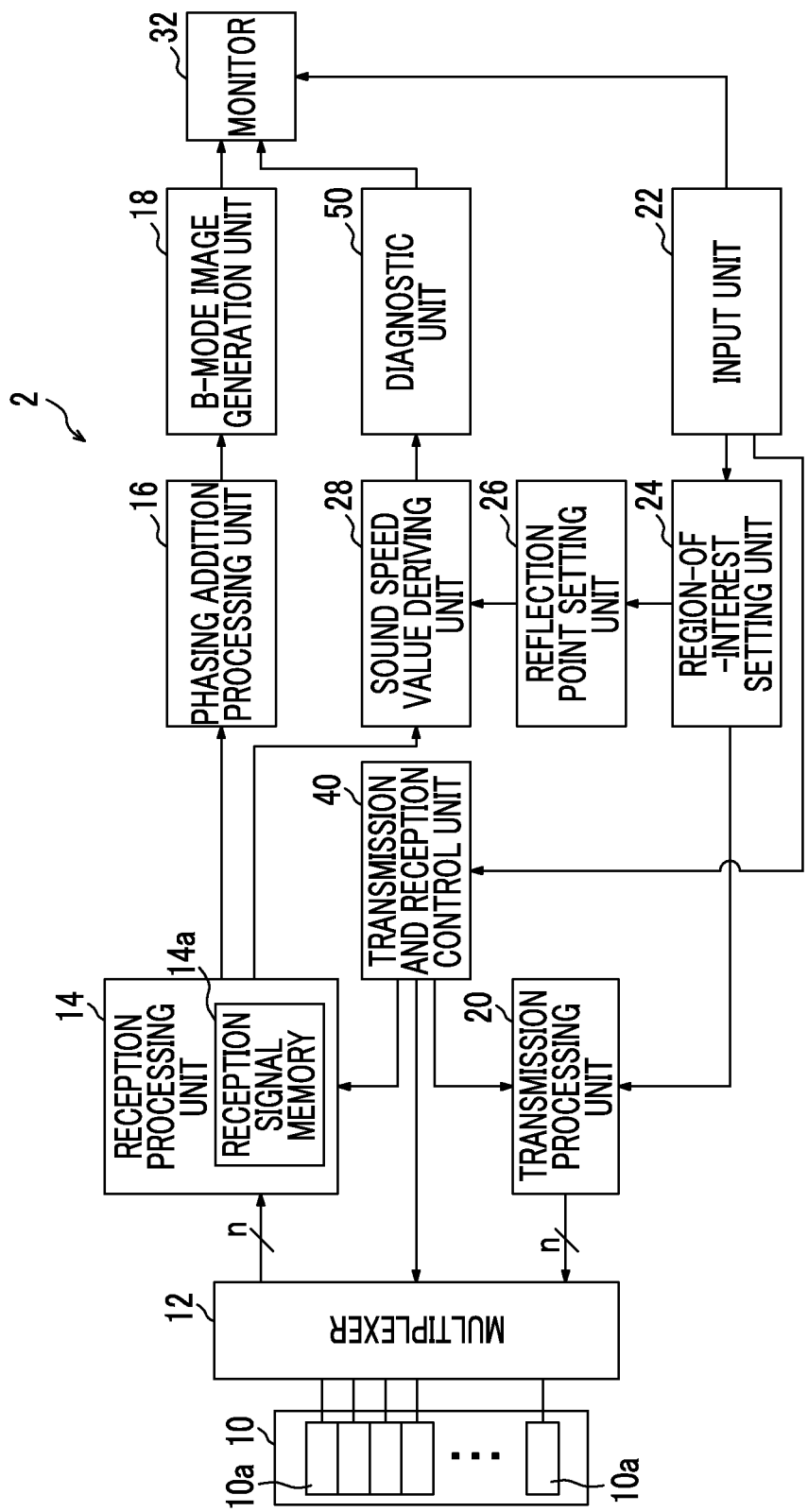
FIG. 12 is a block diagram showing the configuration of an ultrasound diagnostic apparatus according to another embodiment of the present invention.

An ultrasound diagnostic apparatus according to a second embodiment of the present invention will be described below. FIG. 12 is a block diagram showing the configuration of an ultrasound diagnostic apparatus 2 according to the second embodiment of the present invention. In FIG. 12, the same reference numerals are given to the same components as in the ultrasound diagnostic apparatus 1 according to the first embodiment.

The ultrasound diagnostic apparatus 2 according to the second embodiment includes a diagnostic unit 50 instead of the sound speed image generation unit 30 of the ultrasound diagnostic apparatus 1 according to the first embodiment. The diagnostic unit 50 determines the presence of an abnormal part in a region, which is shallower than the depth position of each reflection point in a subject, by analyzing the sound speed value V for each reflection point derived by the sound speed value deriving unit 28. Since other components excluding the diagnostic unit 50 are the same as those of the ultrasound diagnostic apparatus 1 according to the first embodiment, the detailed explanation thereof will be omitted.

Figure 13:
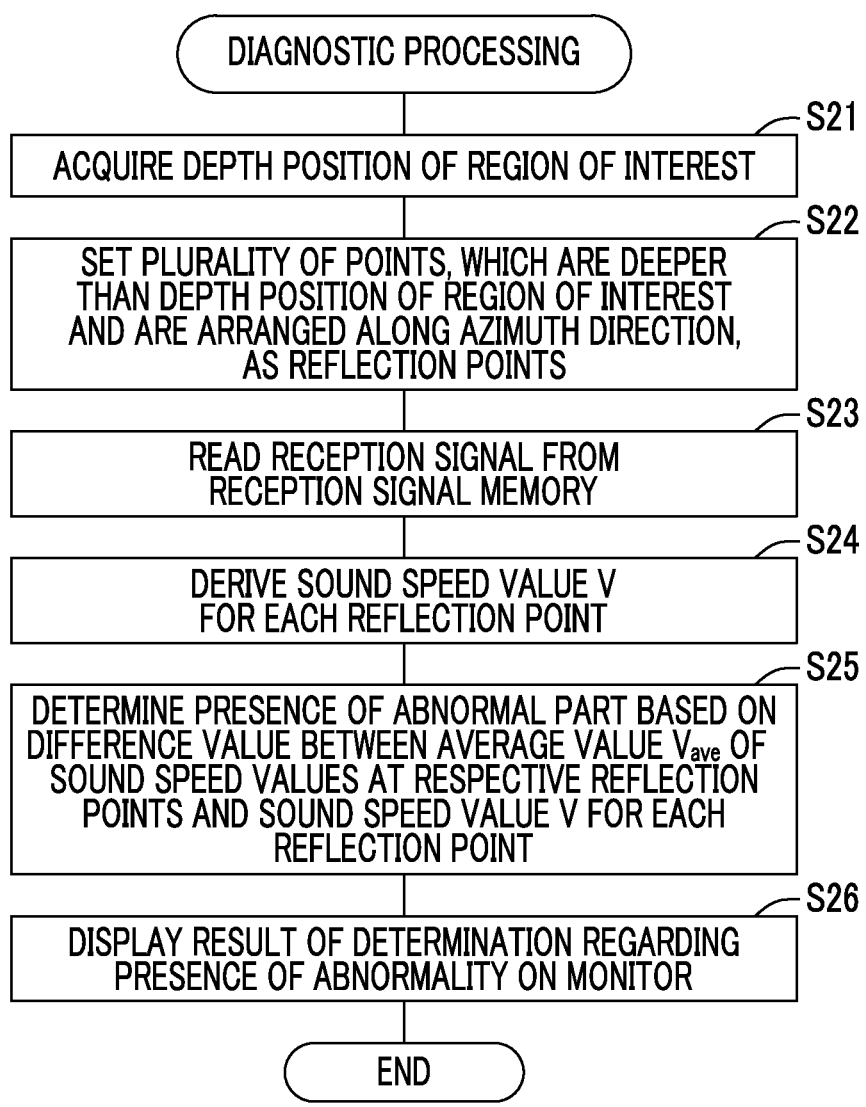
FIG. 13 is a flowchart showing the flow of diagnostic processing performed in the ultrasound diagnostic apparatus according to another embodiment of the present invention.

Hereinafter, a diagnostic process in which the ultrasound diagnostic apparatus 2 according to the second embodiment derives a diagnostic result based on the sound speed value V for each reflection point derived by the sound speed value deriving unit 28 will be described. FIG. 13 is a flowchart showing the flow of the process in a diagnostic processing program executed by the CPU 200 of the ultrasound diagnostic apparatus 2 according to the second embodiment. The diagnostic processing program is stored in the ROM 201 in advance, and is executed, for example, when the user performs a predetermined operation input for the input unit 22. It is assumed that the above-described transmission and reception processing program (refer to FIG. 8) is executed before the diagnostic processing program is executed and a reception signal for deriving the sound speed value V is already stored in the reception signal memory 14a.

When the user designates the depth position of a region of interest in the subject by operating the input unit 22, the region-of-interest setting unit 24 stores data indicating the input depth position of the region of interest in the RAM 202 and supplies the data to the reflection point setting unit 26 in step S21.

In step S22, the reflection point setting unit 26 sets a plurality of points, which are deeper than the depth position of the region of interest notified from the region-of-interest setting unit 24 in step S21, as reflection points for deriving the sound speed value V. As in the first embodiment, the reflection point setting unit 26 sets a plurality of points along a direction in which the piezoelectric elements 10a of the ultrasound probe 10 are aligned (azimuth direction) as reflection points R11 to R17 for deriving the sound speed value V (refer to FIG. 10).

In step S23, the sound speed value deriving unit 28 reads a reception signal corresponding to each scanning line that is stored in the reception signal memory 14a.

In step S24, based on the reception signal of each channel corresponding to each read scanning line, the sound speed value deriving unit 28 derives the sound speed value V according to the above Equation (2) for each of the reflection points R11 to R17 set by the reflection point setting unit 26. The sound speed value deriving unit 28 supplies the sound speed value V for each reflection point to the diagnostic unit 50.

In step S25, the diagnostic unit 50 calculates an average value $V_{ave}$ of the sound speed values V corresponding to the reflection points R11 to R17. Then, when a difference value between the calculated average value $V_{ave}$ and the sound speed value V for each reflection point is equal to or greater than a predetermined threshold value, the diagnostic unit 50 determines that an abnormal part is present at the azimuth position of the reflection point. That is, when the sound speed value corresponding to each reflection point is significantly different from the sound speed values corresponding to the other reflection points, the diagnostic unit 50 determines that an abnormal part is present at the azimuth position of the reflection point.

In step S26, the diagnostic unit 50 supplies information indicating the result of the determination regarding the presence of an abnormal part to the monitor 32. When it is determined that there is an abnormal part, the diagnostic unit 50 supplies information, which indicates the azimuth position of the reflection point corresponding to the abnormal part, to the monitor 32 together with the determination result. As a result, the result of the determination regarding the presence of an abnormal part, such as a torn muscle portion or a tumor, and the azimuth position of the abnormal part are displayed on the monitor 32.

As described above, according to the ultrasound diagnostic apparatus according to the second embodiment of the present invention, the result of the determination regarding the presence of an abnormal part in the subject is displayed on the monitor 32. Therefore, it is possible to perform the detection of an abnormal part more reliably. In addition, in the present embodiment, the case has been exemplified in which the presence of an abnormal part in the subject is determined based on the difference value between the sound speed value V for each reflection point and the average value $V_{ave}$ of the sound speed values V. However, a difference value between the sound speed values V corresponding to two adjacent reflection points may be calculated for each reflection point, and it may be determined that there is an abnormality at the azimuth position of the reflection point when the difference value is larger than a predetermined threshold value.

Figure 14:
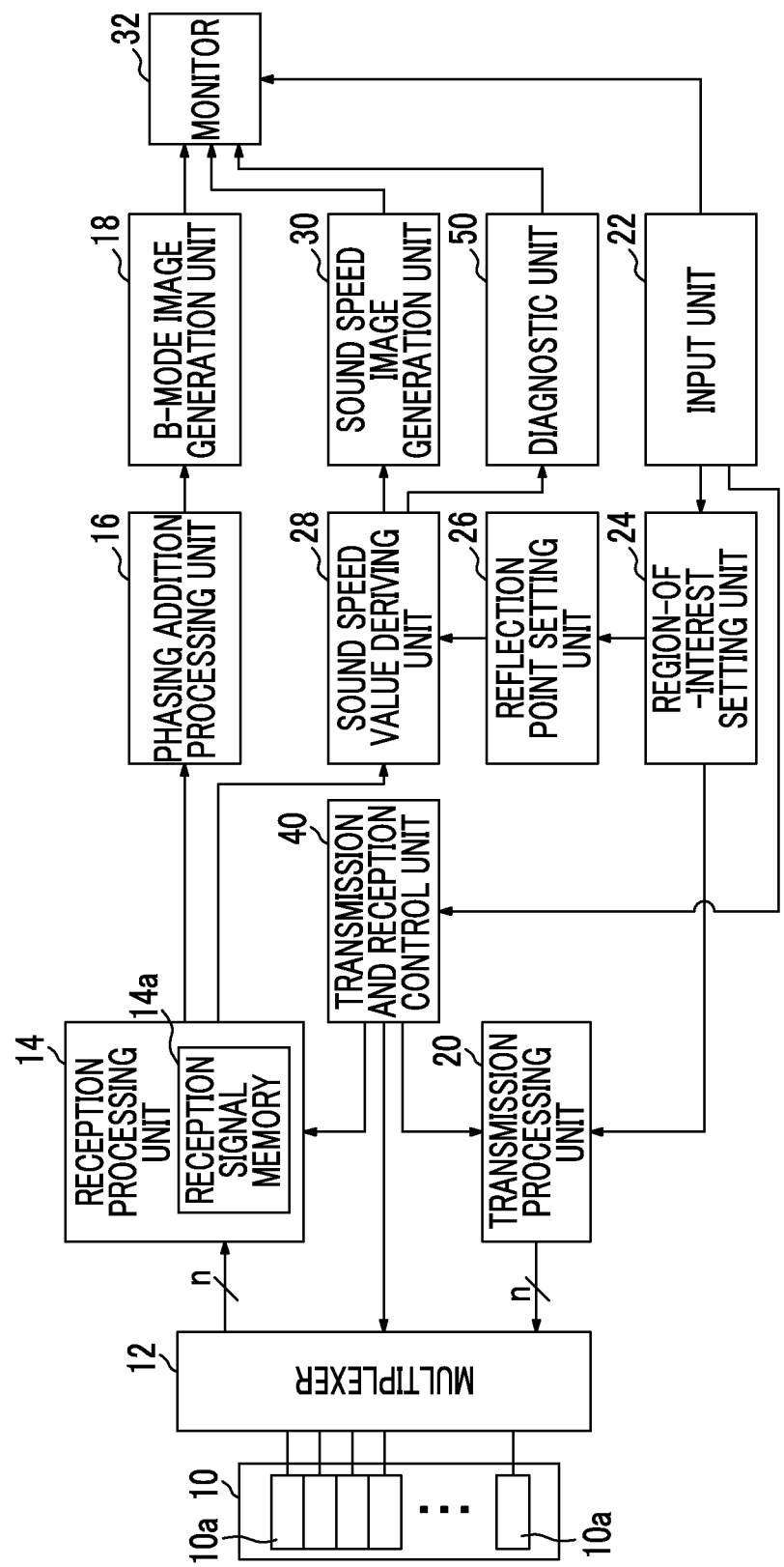
FIG. 14 is a block diagram showing the configuration of the ultrasound diagnostic apparatus according to another embodiment of the present invention.

In addition, as shown in FIG. 14, the diagnostic unit 50 and the sound speed image generation unit 30 may be provided downstream from the sound speed value deriving unit 28, and the sound speed image and the diagnostic result derived by the diagnostic unit 50 may be displayed on the monitor 32.

Third Embodiment

An ultrasound diagnostic apparatus according to a third embodiment of the present invention will be described below. In the following explanation, the configuration of the ultrasound diagnostic apparatus according to the third embodiment is assumed to be the same as in the ultrasound diagnostic apparatus 2 according to the second embodiment shown in FIG. 12, and the detailed explanation of each component will be omitted.

In the ultrasound diagnostic apparatuses according to the first and second embodiments, the reflection point setting unit 26 sets a plurality of points, which are deeper than the depth position of the region of interest and are arranged along a direction in which the piezoelectric elements 10a of the ultrasound probe 10 are aligned (azimuth direction), as reflection points for deriving the sound speed value V. In contrast, in the ultrasound diagnostic apparatus according to the third embodiment, the reflection point setting unit 26 sets a plurality of points, which are deeper than the depth position of the region of interest and are arranged along the depth direction crossing the azimuth direction, as reflection points for deriving the sound speed value V.

Figure 15:
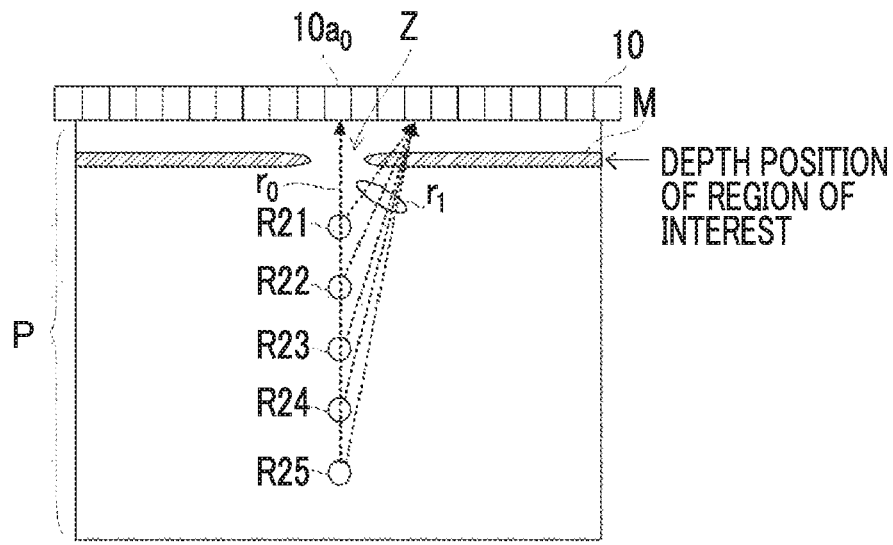
FIG. 15 is a diagram showing the arrangement of reflection points set by a reflection point setting unit according to another embodiment of the present invention.

FIG. 15 is a diagram illustrating the arrangement of reflection points set by the reflection point setting unit 26 in the ultrasound diagnostic apparatus according to the third embodiment. FIG. 15 illustrates a case in which a depth position where the muscle fiber M in the subject P is present is set as the depth position of a region of interest. The reflection point setting unit 26 sets a plurality of points, which are deeper than the depth position of the set region of interest and are arranged along the depth direction, as the reflection points R21 to R25 for deriving the sound speed value V. In the present embodiment, the reflection points R21 to R25 correspond to a plurality of points that are spaced apart from each other at equal intervals on the reception signal generated by the piezoelectric element $10a_0$ located immediately above the reflection points R21 to R25. Although the five reflection points R21 to R25 are shown in FIG. 15, the number of reflection points set by the reflection point setting unit 26 can be appropriately changed.

Hereinafter, diagnostic processing in which the ultrasound diagnostic apparatus according to the present embodiment derives a diagnostic result based on the sound speed value V for each reflection point derived by the sound speed value deriving unit 28 will be described.

Figure 16:
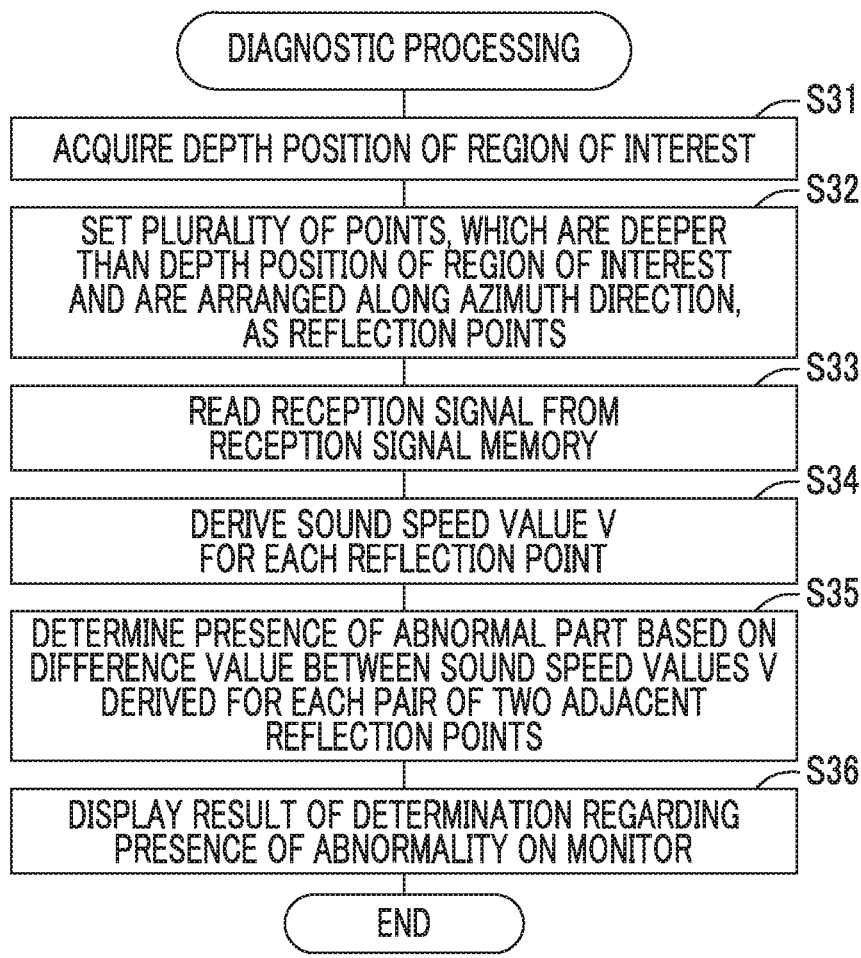
FIG. 16 is a flowchart showing the flow of diagnostic processing performed in the ultrasound diagnostic apparatus according to another embodiment of the present invention.

Hereinafter, diagnostic processing in which the ultrasound diagnostic apparatus 2 according to the third embodiment derives a diagnostic result based on the sound speed value V for each reflection point derived by the sound speed value deriving unit 28 will be described. FIG. 16 is a flowchart showing the flow of the process in a diagnostic processing program executed by the CPU 200 of the ultrasound diagnostic apparatus according to the third embodiment. The diagnostic processing program is stored in the ROM 201 in advance, and is executed, for example, when the user performs a predetermined operation input for the input unit 22. It is assumed that the above-described transmission and reception processing program (refer to FIG. 7) is executed before the diagnostic processing program is executed and a reception signal for deriving the sound speed value V is already stored in the reception signal memory 14a.

When the user designates the depth position of a region of interest in the subject by operating the input unit 22, the region-of-interest setting unit 24 stores data indicating the input depth position of the region of interest in the RAM 202 and supplies the data to the reflection point setting unit 26 in step S31.

In step S32, as shown in FIG. 15, the reflection point setting unit 26 sets a plurality of points along the depth direction, which are deeper than the depth position of the region of interest notified from the region-of-interest setting unit 24, as reflection points for deriving the sound speed value V.

In step S33, the sound speed value deriving unit 28 reads a reception signal corresponding to each scanning line that is stored in the reception signal memory 14a.

In step S34, based on the reception signal of each channel corresponding to each read scanning line, the sound speed value deriving unit 28 derives the sound speed value V according to the above Equation (2) for each of reflection points R21 to R25 (refer to FIG. 15) set by the reflection point setting unit 26. The sound speed value deriving unit 28 supplies the sound speed value V for each reflection point to the diagnostic unit 50.

For example, as shown in FIG. 15, when the reflection points R21 to R25 aligned along the depth direction are located immediately below the torn portion Z of the muscle fiber M, the proportion of each sound speed region on the center path $r_0$ of the ultrasound wave transmitted toward the ultrasound probe 10 from each of the reflection points R21 to R25 is different from the proportion of each sound speed region on the peripheral path $r_1$ (in other words, when the average sound speed value on the center path $r_0$ is different from the average sound speed value on the peripheral path $r_1$). Therefore, as described above, the sound speed value V derived according to Equation (2) increases or decreases as the depth position of the reflection point increases. If the reflection points aligned along the depth direction are located immediately below the muscle fiber M in which the torn portion Z is not generated, the proportion of each sound speed region on the center path $r_0$ of the ultrasound wave transmitted toward the ultrasound probe 10 from each reflection point is approximately the same as the proportion of each sound speed region on the peripheral path $r_1$ (in other words, the average sound speed value on the center path $r_0$ is approximately the same as the average sound speed value on the peripheral path $r_1$). Accordingly, the sound speed value V derived according to Equation (2) converges on a certain value as the depth position of the reflection point increases.

Therefore, in step S35, when the sound speed value V corresponding to each of the reflection points R21 to R25 aligned along the depth position increases or decreases without converging according to the change in the depth position of the reflection point, the diagnostic unit 50 determines that there is an abnormal part at the azimuth position where the reflection points R21 to R25 are aligned. More specifically, the diagnostic unit 50 may derive a difference value between the sound speed values V for each pair of two adjacent reflection points (R21 and R22, R22 and R23, R23 and R24, and R24 and R25), and determine that there is an abnormality at the azimuth position where the reflection points R21 to R25 are aligned when any or all of the difference values are equal to or greater than a predetermined threshold value.

In step S36, the diagnostic unit 50 supplies information indicating the result of the determination regarding the presence of an abnormal part to the monitor 32. When it is determined that there is an abnormal part, the diagnostic unit 50 supplies information, which indicates the azimuth position of the reflection point corresponding to the abnormal part, to the monitor 32 together with the determination result. As a result, the result of the determination regarding the presence of an abnormal part, such as a torn muscle portion or a tumor, and the azimuth position of the abnormal part are displayed on the monitor 32.

In addition, in the above embodiment, the diagnostic unit 50 determines the presence of an abnormal part based on the amount of change in the sound speed value V according to the change in the depth position of the reflection point. However, as will be described below, the diagnostic unit 50 may also determine the presence of an abnormal part based on the amount of change in the apparent distance between the reflection points according to the change in the depth position of the reflection point. In this case, the diagnostic unit 50 derives the apparent depth of each of the reflection points R21 to R25 (apparent distance from the ultrasound probe 10) based on the sound speed value V corresponding to each of the reflection points R21 to R25 derived by the sound speed value deriving unit 28. The apparent depth of each of the reflection points R21 to R25 is obtained by multiplying the sound speed value V derived by the sound speed value deriving unit 28 by the time $T_0$ until the ultrasound wave reflected at each of the reflection points R21 to R25 reaches the piezoelectric element $10a_0$ located immediately above the reflection points R21 to R25. Then, the diagnostic unit 50 calculates an apparent distance between the adjacent reflection points, for each reflection point, based on the apparent depth of each of the reflection points R21 to R25 derived as described above. Then, the diagnostic unit 50 determines that there is an abnormality at the azimuth position where the reflection points R21 to R25 are aligned when the apparent distance between the reflection points increases or decreases by a predetermined threshold value or more according to the depth of the reflection point.

That is, when the proportion of each sound speed region on the center path $r_0$ is the same as the proportion of each sound speed region on the peripheral path $r_1$ (when the average sound speed value on the center path $r_0$ is the same as the average sound speed value on the peripheral path $r_1$), the apparent depth of each reflection point is the same as the true depth. Therefore, the distance between each of the reflection points set at equal intervals and the adjacent reflection point does not change with the change in the depth of the reflection point. On the other hand, when the proportion of each sound speed region on the center path $r_0$ is different from the proportion of each sound speed region on the peripheral path $r_1$ (when the average sound speed value on the center path $r_0$ is different from the average sound speed value on the peripheral path $r_1$), the apparent depth of each reflection point is different from the true depth, and the error increases with the change in the depth of the reflection point. Therefore, the distance between each of the reflection points set at equal intervals and the adjacent reflection point increases or decreases with the change in the depth of the reflection point. Therefore, as described above, it is possible to determine the presence of an abnormal part based on the amount of change in the apparent distance between the reflection points according to the change in the depth position of the reflection point.

Fourth Embodiment

An ultrasound diagnostic apparatus according to a fourth embodiment of the present invention will be described below. In the following explanation, the configuration of the ultrasound diagnostic apparatus according to the fourth embodiment is assumed to be the same as in the ultrasound diagnostic apparatus 1 according to the first embodiment shown in FIG. 1, and the detailed explanation thereof will be omitted. In the ultrasound diagnostic apparatus according to the fourth embodiment, the reflection point setting unit 26 sets a plurality of points, which are deeper than the depth position of the region of interest and are arranged along the azimuth direction and the depth direction, as reflection points for deriving the sound speed value V.

Figure 17:
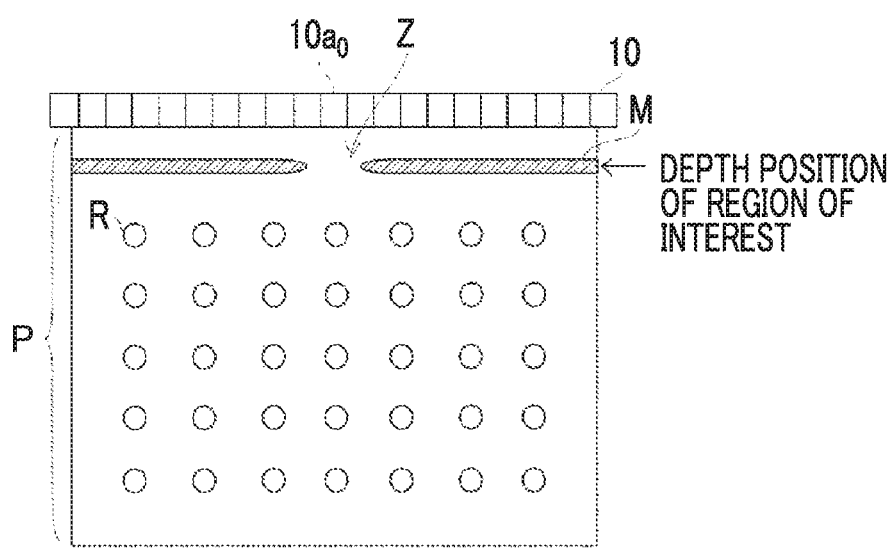
FIG. 17 is a diagram showing the arrangement of reflection points set by a reflection point setting unit according to another embodiment of the present invention.

FIG. 17 is a diagram illustrating the arrangement of reflection points set by the reflection point setting unit 26 in the ultrasound diagnostic apparatus according to the fourth embodiment. FIG. 17 illustrates a case in which a depth position where the muscle fiber M in the subject P is present is set as the depth position of a region of interest. The reflection point setting unit 26 sets a plurality of points, which are deeper than the depth position of the set region of interest and are arranged in a grid pattern along the azimuth direction and the depth direction, as reflection points R for deriving the sound speed value V.

Based on the reception signal of each channel corresponding to each scanning line, the sound speed value deriving unit 28 derives the sound speed value V according to the above Equation (2) for each reflection point R set by the reflection point setting unit 26. The sound speed image generation unit 30 generates an image signal for constructing a sound speed image by assigning a color corresponding to the sound speed value V of each reflection point R to the pixel position of the reflection point, and supplies the image signal to the monitor 32. As a result, a sound speed image in which the sound speed values corresponding to the reflection points arranged in a grid pattern in the subject P have different colors is displayed on the monitor 32.

Thus, according to the ultrasound diagnostic apparatus according to the fourth embodiment, the sound speed value V is derived for each of a plurality of reflection points arranged in a grip pattern along the azimuth direction and the depth direction, and the sound speed image is generated. Therefore, it is possible to specify both the azimuth position and the depth position of an abnormal part, such as a torn muscle portion or a tumor.

In each of the embodiments described above, as a method of deriving the sound speed value at each reflection point, the propagation time $T_0$ of the ultrasound wave passing through the center path $r_0$ from the reflection point R is determined, the propagation time $T_1$ of the ultrasound wave passing through the peripheral path $r_1$ is derived by detecting the signal position corresponding to the same reflection point R on the reception signal of a piezoelectric element spaced apart from the piezoelectric element on the center path $r_0$ by the distance X, and the sound speed value is derived by substituting the propagation times $T_0$ and $T_1$ into Equation (2). However, the method of deriving the sound speed value of each reflection point is not limited to this, and other various known methods can be used.

For example, as another method of deriving the sound speed value V at each reflection point, a method of detecting signal positions corresponding to the same reflection point in the reception signals of a plurality of piezoelectric elements and calculating the sound speed value that best fits these signal positions may be adopted. That is, in this method, $T_1$ in each piezoelectric element is calculated by setting the sound speed value V by giving $T_0$ in Equation (2), and the sound speed value V at which an error between the $T_1$ calculated as described above and $T_1$ detected from the signal is minimized. Such a method of deriving the sound speed value V is disclosed in JP2001-252276A, for example.

In addition, by setting $T_0$ and the sound speed value V for the reception signals of a plurality of piezoelectric elements, the delay time ($T_1$) for each of the reception signals is calculated by Equation (2). Therefore, a method of generating an image signal by performing phasing addition (reception focusing) of the reception signals of the respective piezoelectric elements using the delay time and calculating the sound speed value V at which the sharpness of the image obtained by the image signal is maximized may be adopted as another method of deriving the sound speed value V at each reflection point. Such a method of deriving the sound speed value V is disclosed in JP2007-7045A and JP2008-264531A, for example.

The disclosure of Japanese Patent Application No. 2013-119202 is entirely incorporated in this specification by reference. All documents, patent applications, and technical standards described in this specification are incorporated in this specification by reference to the same extent as when the incorporation of individual documents, patent applications, and technical standards by reference is described specifically and individually.

What is claimed is:

1. An ultrasound diagnostic apparatus, comprising:
an ultrasound probe that transmits an ultrasound wave toward a subject and receives an ultrasound wave, which is reflected from an inside of the subject, to generate a reception signal; and
a processor that is configured to:
set a depth position of a first region, which is a region of interest in the subject;
set a plurality of points in a second region, which is deeper than the depth position of the first region and lies outside of the first region, in the subject, as a plurality of reflection points of ultrasound waves transmitted from the ultrasound probe;
derive a sound speed value in a region between each of the plurality of reflection points and the ultrasound probe, for each of the plurality of reflection points, based on a reception signal generated when the ultrasound probe receives an ultrasound wave reflected at each of the plurality of reflection points; and determine that an abnormality is present in the region of interest of the subject if a difference value, calculated based on the sound speed values derived for the plurality of reflection points in the second region that lies outside of the first region, is equal to or greater than a predetermined threshold value, wherein the difference value is calculated by either:

calculating a difference between a sound speed value derived for a reflection point and an average sound speed value calculated over the plurality of reflection points, or calculating a difference between a sound speed value derived for a first reflection point and a sound speed value derived for another reflection point that is different from the first reflection point.

2. The ultrasound diagnostic apparatus according to claim 1, wherein the processor is further configured to display each sound speed value on a display screen.

3. The ultrasound diagnostic apparatus according to claim 2, wherein the processor is configured to generate a sound speed image in which sound speed values are displayed in different colors according to magnitude of the sound speed value.

4. The ultrasound diagnostic apparatus according to claim 1, wherein:
the processor is configured to derive a diagnostic result for the region of interest based on each sound speed value.

5. The ultrasound diagnostic apparatus according to claim 4, wherein the processor is configured to set, as reflection points, a plurality of points along an azimuth direction parallel to an ultrasound wave transmitting and receiving surface of the ultrasound probe.

6. The ultrasound diagnostic apparatus according to claim 5, wherein the processor is configured to derive a diagnostic result based on an average value of the sound speed values, which are derived for the plurality of reflection points, and based on the sound speed value derived for each of the plurality of reflection points.

7. The ultrasound diagnostic apparatus according to claim 4, wherein the processor is configured to set, as reflection points, a plurality of points along a depth direction crossing an ultrasound wave transmitting and receiving surface of the ultrasound probe.

8. The ultrasound diagnostic apparatus according to claim 7, wherein the processor is configured to derive a difference value between sound speed values for each of at least one or more pairs of two different reflection points among the plurality of reflection points, and derives a diagnostic result based on the derived difference value.

9. The ultrasound diagnostic apparatus according to claim 4, wherein the processor is configured to set, as reflection points, a plurality of points along an azimuth direction parallel to an ultrasound wave transmitting and receiving surface of the ultrasound probe and a depth direction crossing the azimuth direction.

10. The ultrasound diagnostic apparatus according to claim 1, wherein the processor is configured to set, as reflection points, a plurality of points along an azimuth direction parallel to an ultrasound wave transmitting and receiving surface of the ultrasound probe.

11. The ultrasound diagnostic apparatus according to claim 10, wherein the ultrasound probe includes a plurality of electro-acoustic transducers disposed at different positions, and the processor is configured to derive a sound speed value corresponding to each reflection point based on a time until an ultrasound wave reflected at a set reflection point is received by each of the electro-acoustic transducers.

12. The ultrasound diagnostic apparatus according to claim 1, wherein the processor is configured to set, as reflection points, a plurality of points along a depth direction crossing an ultrasound wave transmitting and receiving surface of the ultrasound probe.

13. The ultrasound diagnostic apparatus according to claim 12, wherein the ultrasound probe includes a plurality of electro-acoustic transducers disposed at different positions, and the processor is configured to derive a sound speed value corresponding to each reflection point based on a time until an ultrasound wave reflected at a set reflection point is received by each of the electro-acoustic transducers.

14. The ultrasound diagnostic apparatus according to claim 1, wherein the processor is configured to set, as reflection points, a plurality of points along an azimuth direction parallel to an ultrasound wave transmitting and receiving surface of the ultrasound probe and a depth direction crossing the azimuth direction.

15. The ultrasound diagnostic apparatus according to claim 14, wherein the ultrasound probe includes a plurality of electro-acoustic transducers disposed at different positions, and the processor is configured to derive a sound speed value corresponding to each reflection point based on a time until an ultrasound wave reflected at a set reflection point is received by each of the electro-acoustic transducers.

16. The ultrasound diagnostic apparatus according to claim 1, wherein the ultrasound probe includes a plurality of electro-acoustic transducers disposed at different positions, and the processor is configured to derive a sound speed value corresponding to each reflection point based on a time until an ultrasound wave reflected at a set reflection point is received by each of the electro-acoustic transducers.

* * * * *